(12) United States Patent
Huffstutler

(10) Patent No.: US 10,928,617 B1
(45) Date of Patent: Feb. 23, 2021

(54) PORTABLE THREE-DIMENSIONAL VIRTUAL IMAGING DEVICE

(71) Applicant: Gary D. Huffstutler, Portsmouth, VA (US)

(72) Inventor: Gary D. Huffstutler, Portsmouth, VA (US)

(73) Assignee: GDH Enterprises, LLC, Portsmouth, VA (US)

( * ) Notice: Subject to any disclaimer, the term of this patent is extended or adjusted under 35 U.S.C. 154(b) by 16 days.

(21) Appl. No.: 16/416,813

(22) Filed: May 20, 2019

Related U.S. Application Data

(60) Provisional application No. 62/673,469, filed on May 18, 2018.

(51) Int. Cl.
| | | |
|---|---|---|
| *G02B 21/00* | (2006.01) | |
| *G02B 21/36* | (2006.01) | |
| *H04N 5/33* | (2006.01) | |
| *H04N 5/225* | (2006.01) | |
| *H04N 5/232* | (2006.01) | |
| *H04N 13/15* | (2018.01) | |

(Continued)

(52) U.S. Cl.
CPC ....... *G02B 21/008* (2013.01); *G02B 21/0076* (2013.01); *G02B 21/36* (2013.01); *G02B 21/362* (2013.01); *H04N 5/2253* (2013.01); *H04N 5/23299* (2018.08); *H04N 5/247* (2013.01); *H04N 5/332* (2013.01); *H04N 13/15* (2018.05); *H04N 2013/0081* (2013.01)

(58) Field of Classification Search
CPC .. G02B 21/008; G02B 21/0076; G02B 21/36; G02B 21/362; H04N 13/15; H04N 5/23299; H04N 5/2253; H04N 5/247; H04N 5/332; H04N 2013/0081
See application file for complete search history.

(56) References Cited

U.S. PATENT DOCUMENTS

| | | |
|---|---|---|
| 5,420,427 A | 5/1995 | Morgan et al. |
| 6,615,063 B1 | 9/2003 | Ntziachristos et al. |

(Continued)

FOREIGN PATENT DOCUMENTS

| | | |
|---|---|---|
| CN | 101936904 A | 1/2011 |

OTHER PUBLICATIONS

An Operational Near-Infrared Fluorescence Imaging System Prototype for Large Animal Surgery,Technology in Cancer Research & Treatment, Dec. 2003, pp. 1-10, vol. 2, No. 6, Adenine Press (2003), U.S.

(Continued)

*Primary Examiner* — Blake C Riddick
(74) *Attorney, Agent, or Firm* — Williams Mullen; Douglas C. Tsao

(57) ABSTRACT

A portable imaging system. The imaging system uses perpendicular beams, both low level laser beams at $TEM_{00}$ Mode and infrared laser beams all beams at a different level, to separate multipliers to provide bodily Fourier Transformed analog signals, gain, and then separate filters to improve signal quality, and a charge-coupled Device (CCD) to convert the analog signals to digital signals. These separate signal sets are then stored, and a program converts the signals to a rotatable, section capable translucent digital image. The imaging medium for the process may be low concentration Indocyanine Green Dye.

18 Claims, 40 Drawing Sheets

(51) Int. Cl.
*H04N 5/247* (2006.01)
*H04N 13/00* (2018.01)

(56) References Cited

U.S. PATENT DOCUMENTS

| | | | |
|---|---|---|---|
| 6,678,764 | B2 | 1/2004 | Parvulescu et al. |
| 6,889,075 | B2 | 5/2005 | Marchitto et al. |
| 9,044,142 | B2 | 6/2015 | Hauger et al. |
| 9,414,749 | B2 | 8/2016 | Semenov |
| 9,672,471 | B2 | 6/2017 | Boyden et al. |
| 2004/0178356 | A1* | 9/2004 | Natori ............... G02B 21/0064 250/458.1 |
| 2007/0086005 | A1* | 4/2007 | Gfrorer ............... G01N 21/64 356/318 |
| 2007/0097369 | A1* | 5/2007 | Shimada ............ G01N 21/6456 356/417 |
| 2008/0177184 | A1* | 7/2008 | Goldman ............... A61B 5/489 600/476 |
| 2008/0254499 | A1* | 10/2008 | Low .................... A61K 47/542 435/29 |
| 2009/0250628 | A1* | 10/2009 | Mano ................. G02B 21/0076 250/458.1 |
| 2009/0270718 | A1* | 10/2009 | Peter .................. G01R 33/4808 600/411 |
| 2011/0071388 | A1 | 3/2011 | Yared et al. |
| 2011/0242308 | A1* | 10/2011 | Igarashi ................ G02B 21/34 348/79 |
| 2013/0243151 | A1 | 9/2013 | Shih |
| 2016/0038029 | A1* | 2/2016 | Darne ................. A61B 5/0071 600/427 |
| 2017/0215826 | A1 | 8/2017 | Johnson et al. |
| 2018/0266958 | A1* | 9/2018 | Hufnagel .......... G01N 21/6402 |
| 2018/0319102 | A1* | 11/2018 | Kurtz .................... B29C 70/462 |
| 2019/0384047 | A1* | 12/2019 | Johnson ............... G06K 9/3233 |

OTHER PUBLICATIONS

John W. Kakareka, Nicole Y. Morgan, Makoto Mitsunaga, Thomas J. Pohida, Nobuyuki Kosaka, Thomas E. McCann, Peter L. Choyke, Hisataka Kobayashi, A Portable Fluorescence Camera for Testing Surgical Specimens in the Operating Room: Description and Early Evaluation, Molecular Imaging Biology, Oct. 20, 2010, pp. 862-867, U.S.

Susan L. Troyan, M.D., Vida Kianzad, Ph.D., Summer L. Gibbs-Strauss, Ph.D., Sylvain Gioux, M.E., Aya Matsui, M.D., Rafiou Oketokoun, M.S., Long Ngo, Ph.D., Ali Khamene, Ph.D., Fred Azar, Ph.D., John V. Frangioni, M.D., Ph.D., The FLARE Intraoperative Near-Infrared Fluorescence Imaging System: A First-in-Human Clinical Trial in Breast Cancer Sentinel Lymph Node Mapping, Annals of Surgical Oncology, Oct. 2009, pp. 2943-2952, National Institutes of Health, Author Manuscript, U.S.

Paul Dorval, Norman Mangeret, Stephanie Guillermet, Christian Righini, Gabriele Barabino, Philippe Rizo, Patrick Poulet, The Fluostick, a real hand-held system for near-infrared fluorescence image-guided surgery, Proceedings of SPIE, Advanced Biomedical and Clinical Diagnostic and Surgical Guidance Systems XII, 2014, vol. 8935, U.S.

Sarah J. Erickson, Sergio L. Martinez, Joseph Decerce, Adrian Romero, Lizeth Caldera, Anuradha Godavarty, Three-dimensional fluorescence tomography of human breast tissues in vivo using a hand-held optical imager, Physics in Medicine and Biology, 2013, pp. 1563-1579, vol. 58, IOP Publishing, U.S.

Benjamin A. Flusberg, Eric D. Cocker, Wibool Piyawattanametha, Juergen C. Jung, Eunice L. M. Cheung, Mark J. Schnitzer, Fiber-optic fluorescence imaging, National Institutes of Health, Author Manuscript, Dec. 2005, Nature Publishing Group, U.S.

Michael J. Sanderson, Ian Parker, Martin D. Bootman, Fluorescence Microscopy, Jan. 13, 2016, Department of Health Human Services Author Manuscript, U.S.

Thomas J. Fellers, Michael W. Davidson (Mar. 21, 2016). Introduction to Confocal Microscopy. Retrieved from web.archive.org/web/20160321051202/http://olympus.magnet.fsu.edu/primer/techniques/confocal/confocalintro.html on Aug. 5, 2019.

Colin J. R. Sheppard, Multidimensional Microscopy, 1994, pp. 1-31, Springer-Verlag New York, U.S.

Ernst H. K. Stelzer, Multidimensional Microscopy, 1994, pp. 33-51, Springer-Verlag New York, U.S.

Andres Kriete, Multidimensional Microscopy, 1994, pp. 209-230, Springer-Verlag New York, U.S.

Jagath K. Samarabandu, Raj Acharya, Ping-Chin Cheng, Multidimensional Microscopy, 1994, pp. 231-250, Springer-Verlag New York, U.S.

Eric S. Boxall, Nick S. White, Gerald S. Benham, Multidimensional Microscopy, 1994, pp. 251-266, Springer-Verlag New York, U.S.

Anna Smallcombe, Gerald S. Benham, Multidimensional Microscopy, 1994, pp. 267-289, Springer-Verlag New York, U.S.

\* cited by examiner

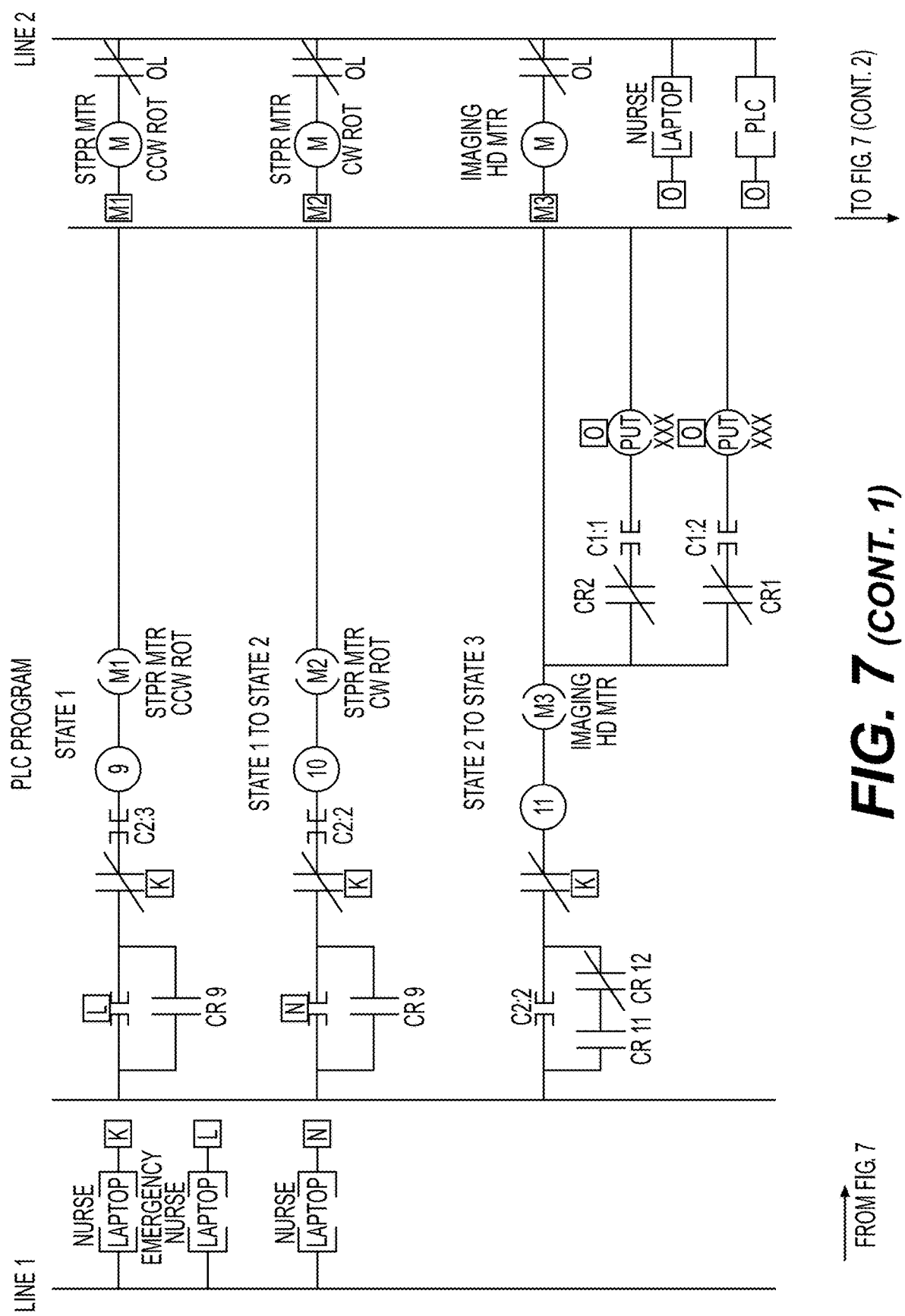
FIG. 7 (CONT. 1)

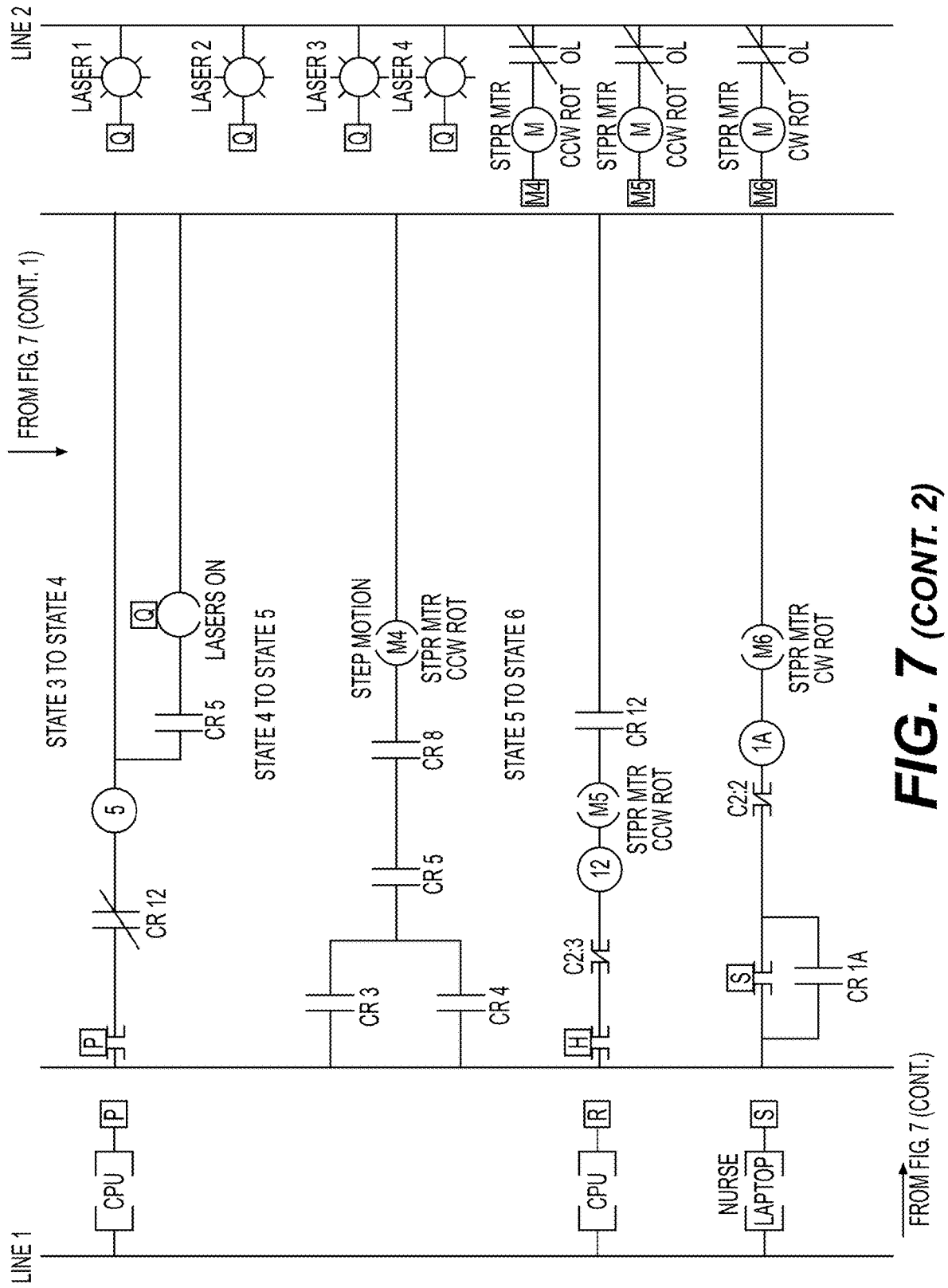
FIG. 7 (CONT. 2)

NURSE

Agent – component, person, program etc. working to achieve a primary goal.

| Agent Code | Name |
|---|---|
| Br | Brake |
| IM | Imaging Head Motor |
| L | Laptop |
| LM | Laser Distance Measurer |
| N | Nurse |
| P | Patient |
| PLC | Programmable Logic Controller |
| Pr | Program |
| S | Sensor |
| SM | Stepper Motor |
| T | Tachometer |

PORTABLE THREE-DIMENSIONAL VIRTUAL IMAGING DEVICE

CROSS-REFERENCE TO RELATED APPLICATIONS

This application claims the benefit of priority to U.S. Provisional Patent Application No. 62/673,469, filed May 18, 2018.

STATEMENT REGARDING FEDERALLY SPONSORED RESEARCH OR DEVELOPMENT

Not Applicable

FIELD

This invention relates generally to veterinary and medical imaging providing physicians, surgeons, and veterinarians with virtual images of the internal organs, masses, etc. of their patients.

BACKGROUND

Currently, medical imaging systems, even movable ones are often heavy and can only be rolled around within a hospital setting. Usually, hospitals in remote areas do not have medical imaging capability. Surgeons and other physicians who travel overseas to do medical work do not have reference images for their work.

Another problem concerning medical imaging is the limited ability to deal with patients who have devices such as pacemakers. Currently, the only imaging option for a person with a pacemaker or similar device is a computed tomography (CT) scan, unless the patient has a magnetic resonant imaging (MRI) capable device installed. Normally, surgeons and physicians prefer MRIs over CT scans. If a CT scan is to image soft tissue, a nuclear imaging medium may have to be introduced intravenously in order for the image to show the soft tissue such as a positron emission tomography (PET) scan.

Also, many veterinarians travel to farms outside of their office to service farm animals. These animals are expensive to purchase and support, yet they are an important part of the national food supply. It would be desirable to have an imaging system that could easily travel with a veterinarian or physician for scanning a subject onsite, while at the same time, not relying on the use of nuclear imaging mediums for generating images.

BRIEF SUMMARY

The imaging system of the present disclosure is adapted to produce a three-dimensional image of a subject along a longitudinal y-axis and a cross section along x-z axes. The imaging system may operate by scanning a subject (e.g., a living animal or human) with a portable imaging system comprising a 90° crisscrossed fluorescent confocal and 90° crisscrossed infrared methods with the separate beams at slightly different level or positions from each other, and the associated motherboard and program producing a rotatable and virtual translucent three dimensional (3-D) image that shows structures within the living body that is shown on a normal laptop display screen. The fluorescent confocal parts and the infrared parts may be rotated circumferentially around the subject via an electrically motorized gearing or V-belt, and the entire rotating confocal and infrared assembly may be moved along the animal or patient's body linearly via an electrically powered lead (power) screw assembly.

The subject is given intravenously a U.S. Food and Drug Administration (FDA) approved non-nuclear medium, such as a low concentration medium of Indocyanine Green Dye. This non-nuclear medium is used for fluorescence-enhanced imaging given by the crisscrossed fluorescent confocal beams. This medium improves the 3-D image clarity.

Thermography uses heat from a body to generate images that can assist a physician or veterinarian in making a diagnosis. For example, thermal imagers have been used for the detection of breast cancer as well as musculoskeletal and circulatory disorders.

The imaging system described herein is adapted to be portable enabling a surgeon or physician overseas to easily travel with the imaging system. For example, the imaging system may be carried on-flight overseas. The imaging system may be adapted to be easily assembled or dismantled, placed in a flight container that is U.S. Transportation Security Administration (TSA) approved and acceptable to airline companies meeting their normal baggage weight restrictions, and then the system preferably can be easily reassembled and used overseas on-site. The imaging system may also easily be taken by a veterinarian to a site such as a farm, easily reassembled and used on-site. After use, the system can then easily be disassembled and placed in a container for the next use.

In one embodiment, the imaging system comprises an image processing system, a first confocal fluorescent microscopy assembly, a second confocal microscopy assembly, a first thermographic assembly and a second thermographic assembly. The image processing system includes a computer processor and memory. Each confocal fluorescent microscopy assembly includes a fluorescent laser emitting an incident light, a beam splitter to receive the fluorescence and direct a transmission portion along an optical path, and an optical filter assembly in operable engagement with the transmission portion and delivering a filtered transmission portion along an optical path to a detector assembly. The beam splitters and filters are chosen to match one or more predetermined fluorophores, such as indocyanine green dye. Each thermographic assembly includes a thermographic camera.

The image processing system, first and second confocal microscopy assemblies, and first and second thermographic assemblies are housed in a rotatable and longitudinally extensible mount assembly. The mount assembly is disposed about the y-axis of the subject, and configured to rotate imaging elements engaged with the mount assembly relatively about the y-axis of the subject. The mount assembly is also configured to move imaging elements engaged with the mount assembly relatively along the y-axis of the subject. The mount assembly includes a controller configured to control such rotational and extensible movement of the mount assembly and to communicate a relative rotational and extensible movement value to the image processing system.

The mount assembly may be substantially ring-shaped and having an internal diameter. It is understood that by describing embodiments of the mount assembly as substantially ring-shaped, the mount assembly need not adopt a strict circular profile. Embodiments of the mount assembly that are substantially ring-shaped merely adopt a shape that sufficiently encircles the subject to enable the approximate configuration of the various imaging elements as disclosed.

The first and second confocal fluorescent microscopy assemblies are engaged with the mount assembly in relative orthogonal geometry about the subject so that the first and second optical paths cross substantially at the y-axis and are configured to generate image data of the subject. The first and second confocal fluorescent microscopy assemblies are adapted to be rotatable and extensible about the subject in consistent relative geometry. Similarly, the first and second thermographic assemblies are engaged with the mount assembly in relative orthogonal geometry about the subject so as to be configured to image the subject with crossing thermally optical paths (at slightly different levels to avoid excess energy within the flesh at any one point). The first and second thermographic assemblies are adapted to be rotatable and extensible about the subject in consistent relative geometry.

The image processing system is in operable communication with the fluorescent microscopy assemblies and thermographic assemblies. Both the detector assemblies and the thermographic cameras are configured to communicate digital image values to the image processing system.

The computer processor of the image processing system is specifically configured so as to process digital image values from the detection assemblies and thermal cameras, with both in correlated association with the relative rotation and translation value from the controller so as to generate a three-dimensional voxel of the subject from rotational and extensible movement of the mount about the subject. The three-dimensional voxel contains spatially associated thermal data.

In one embodiment, the mount assembly is configured to longitudinally extend along a vertical axis. In an alternative embodiment, the mount assembly is configured to extend along a horizontal axis.

The internal diameter of the mount assembly may vary. For example, the internal diameter may be about 25 inches. In another example, the internal diameter is 36 inches.

The mount assembly may be configured to rotate imaging elements engaged with the mount assembly via an electrically motorized gearing. In another embodiment, the mount assembly is configured to rotate the imaging elements with a V-belt.

In one embodiment, the mount assembly may be configured to move imaging elements engaged with the mount relatively along the y-axis via an electrically powered lead screw assembly. For example, the electrically powered lead screw assembly may be comprised of a lead screw assembly powered by a stepper motor.

The imaging system may further include a tachometer configured to measure a rotational speed of the imaging elements and provide the rotational speed to the controller. A brake may be included to lower the rotational speed of the imaging elements.

The mount assembly may comprise a base having a lead screw assembly extending along the y-axis and a rotatable mount adapted to move along the lead screw assembly. In one embodiment, the base and the mount are substantially parallel and the lead screw assembly is vertically oriented, whereby the mount moves along a vertical axis. In another embodiment, the base and the mount are substantially perpendicular and the lead screw assembly is horizontally oriented, whereby the mount moves along a horizontal axis.

DETAILED DESCRIPTION

Figure 1:
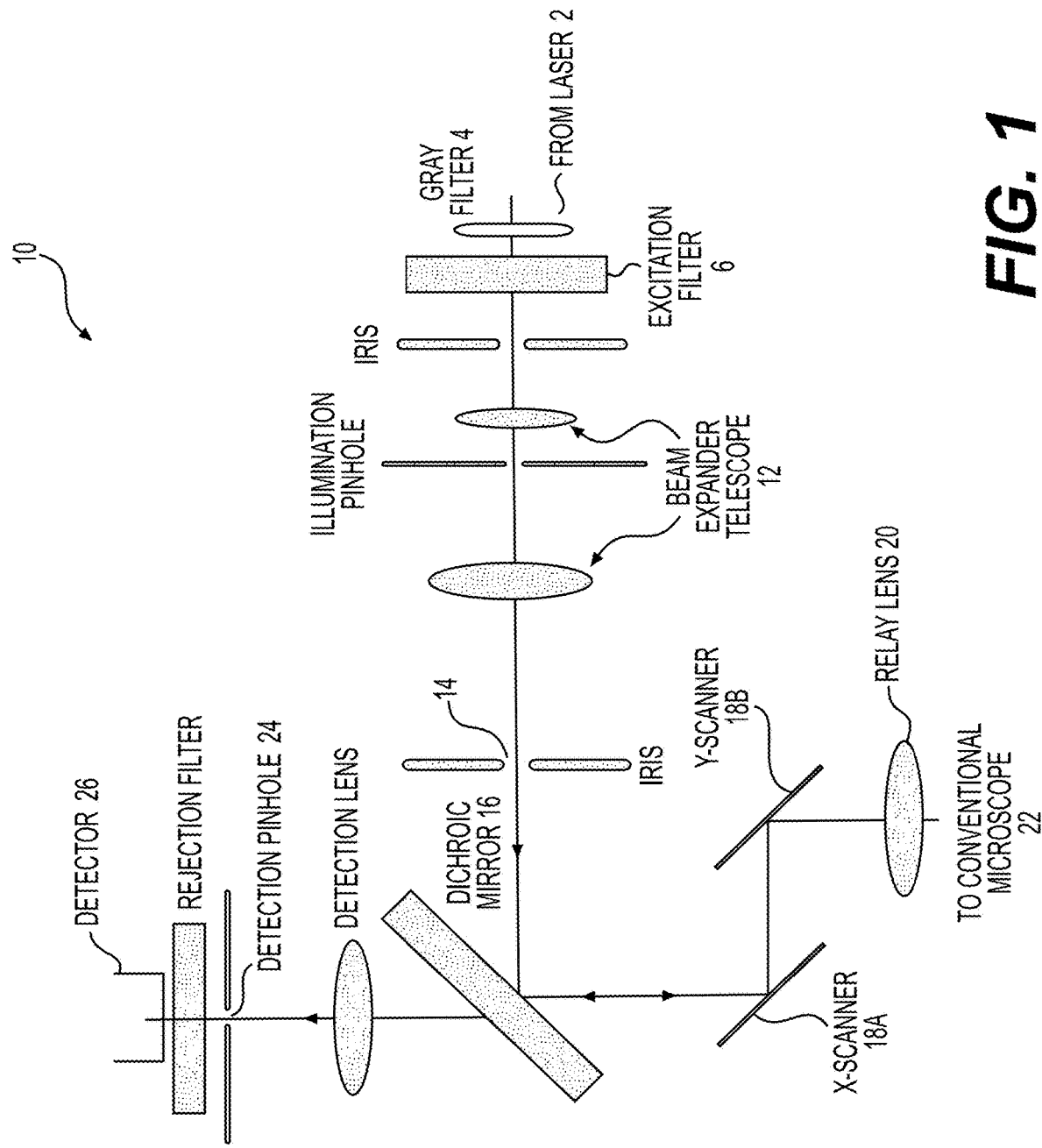
FIG. 1 is a schematic of a fluorescent confocal scanning imaging system.

Embodiments of the system may now be described more fully with reference to the accompanying drawings, in which embodiments of the system are shown. However, this invention should not be construed as limited to the embodiments set forth herein. Rather, these embodiments are provided so that this disclosure will be thorough and complete, and will fully convey the scope of the invention to those skilled in the art.

As used herein, the term "comprising" or "comprises" is open-ended, and includes one or more stated features, integers, elements, steps, components or functions but does not preclude the presence or addition of one or more other features, integers, elements, steps, components, functions or groups thereof. As used herein, the term "and/or" includes any and all combinations of one or more of the associated listed items. The term "about" means the stated value plus or minus a reasonable or conventional margin of error of measurement, or plus or minus 10% if no method of measurement is indicated.

As used herein, the common abbreviation "e.g.," which derives from the Latin phrase "exempli gratia," may be used to introduce or specify a general example or examples of a previously mentioned item and is not intended to be limiting of such item. If used herein, the common abbreviation "i.e.," which derives from the Latin phrase "id est," may be used to specify a particular item from a more general recitation.

The terminology used herein is for the purpose of describing particular embodiments only and is not intended to be limiting of the invention. As used herein, the singular forms "a," "an" and "the" are intended to include the plural forms as well, unless the context clearly indicates otherwise.

Well-known functions or constructions may not be described in detail for brevity and/or clarity. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In addition, spatially relative terms, such as "under," "below," "lower," "over," "upper," "downward," "upward," "inward, "outward" and the like, may be used herein for ease of description to describe one element or feature's relationship to another element(s) or feature(s) as illustrated in the figures. It will be understood that the spatially relative terms are intended to encompass different orientations of the imaging system in use or operation in addition to the orientation depicted in the figures. For example, if the imaging system in the figures is turned over, elements described as "under" or "beneath" other elements or features would then be oriented "over" the other elements or features. Thus, the exemplary term "under" can encompass both an orientation of over and under. The imaging system may be otherwise oriented (rotated 90 degrees or at other orientations) and the spatially relative descriptors used herein interpreted accordingly.

It will be understood that when an element is referred to as being "attached," "coupled" or "connected" to another element, it can be directly attached, coupled or connected to the other element or intervening elements may also be present. In contrast, when an element is referred to as being "directly attached," directly coupled" or "directly connected" to another element, there are no intervening elements present. Words such as passageway, fluid path, or flow component, etc., are intended to communicate structure supporting fluid communication and may comprise a tube, pipe, hose, boring, channel, etc.

The imaging system may take a variety of dimensions, depending on the application, including subject size and detection target. Two commonly useful models of the imaging system may include: 1) a first model having a patient space with a 25-inch internal diameter, and 2) a second model having a patient space with a 36-inch internal diameter. One model has an internal 25-inch diameter stands vertically and has vertical movement of the imaging head. The model with the internal 36-inch diameter may lie on a horizontal (e.g., a base on the ground) and has horizontal movement of the imaging head. Both model sizes perform the same imaging functions.

Both models may have two sets of fluorescent confocal laser-beam splitter assemblies and associated detection assemblies. Both models may also have sets of infrared laser assemblies with associated detection assemblies. Each specific type of set may have the second assembly and detection assembly substantially at right angles to the first assembly and detection assembly. Each detection assembly may have associated filters and a charge-coupled device (CCD) that in the scanning process continually send images to a programmable logic controller (PLC). The detection assemblies send analog signals which are improved by their respective filters and the CCDs convert the analog signals to digital signals. Because the beams have widths, and are at right angles to each other, the beams form the four legs of a square. The height may be provided by an incremental height change provided by a lead screw and a stepper motor. This gives a digital volume which is normally called a "voxel."

The subject is given intravenously a U.S. Food and Drug Administration (FDA) approved non-nuclear medium, such as a low concentration medium of Indocyanine Green Dye. Lasers used in the imaging system are small and lightweight and emit wavelengths in the 500-950 nm range. Two of the laser beams may be either infrared or near-infrared in nature. One embodiment of the beam splitter is a dichroic mirror having a hard clear short solid cylinder with opposing spherical ends. The beam splitter may further include one or more coatings (either hard or soft) that may also act as filtering agents.

Rotation of the laser sets, which may be sitting on a rotatable mount, around the patient is provided by a v-belt or gear and an imaging head servo-motor. The PLC may have two receiving memory stations that receive the digital signals from the CCDs. As shown, there is an outer trip on the rotatable mount, that causes sensor to send a message to the PLC where a programmed toggle in the PLC causes the PLC to swap receiving memory stations, and then dump the previous memory digital data to the memory of a motherboard that has the imaging program installed within. A tachometer or like device may provide the rotational speed data to the PLC; a brake or similar device may stop the rotation of the rotatable mount once the scan is complete.

The motherboard may then take the digital data and converts the data into two sets of virtual 3-D images one fluorescent confocal and the other infrared confocal. Once both 3-D images are complete, the infrared 3-D image will be overlaid onto the fluorescent confocal image. This total image will be rotatable, will be capable of slicing the image at any angle, capable of providing a volumetric measurement of any specific object within the image, provide a distance measurement between objects within the image, and provide a temperature reading at depth of any specific object within the image. Once the 3-D image is formed, the imaging system may prompt an operator to write the image to either a suitable memory, such as CD-ROM or a memory stick as desired, at the time. A laptop, for example, may also have the program installed on it so that the image can be reviewed by the physician on the laptop screen at a later time.

FIG. 1 provides one example of a confocal microscope arrangement adapted for use within the imaging system. The laser light 2 centers the instrument 10 from the right side. A set of grey filters 4 is used to attenuate the laser power and an excitation filter 6 selects a single line. The beam is expanded in the telescope (using beam expander telescope 12) and spatially filtered with a pinhole 14. The beam splitter 16 deflects the expanded beam towards a scanner unit (comprising x-scanner 18a and y-scanner 18b) and the relay lens 20 focuses the beam into the primary image plane of the attached conventional microscope 22. The emitted fluorescent light is "descanned," passes the beam splitter 16, is focused into a pinhole 24 and detected with a photomultiplier 26 as a function of the scanner tilt angles. The two irises define the optical path of the instrument. All optical elements use these as references while the instrument is arranged.

Figure 2:
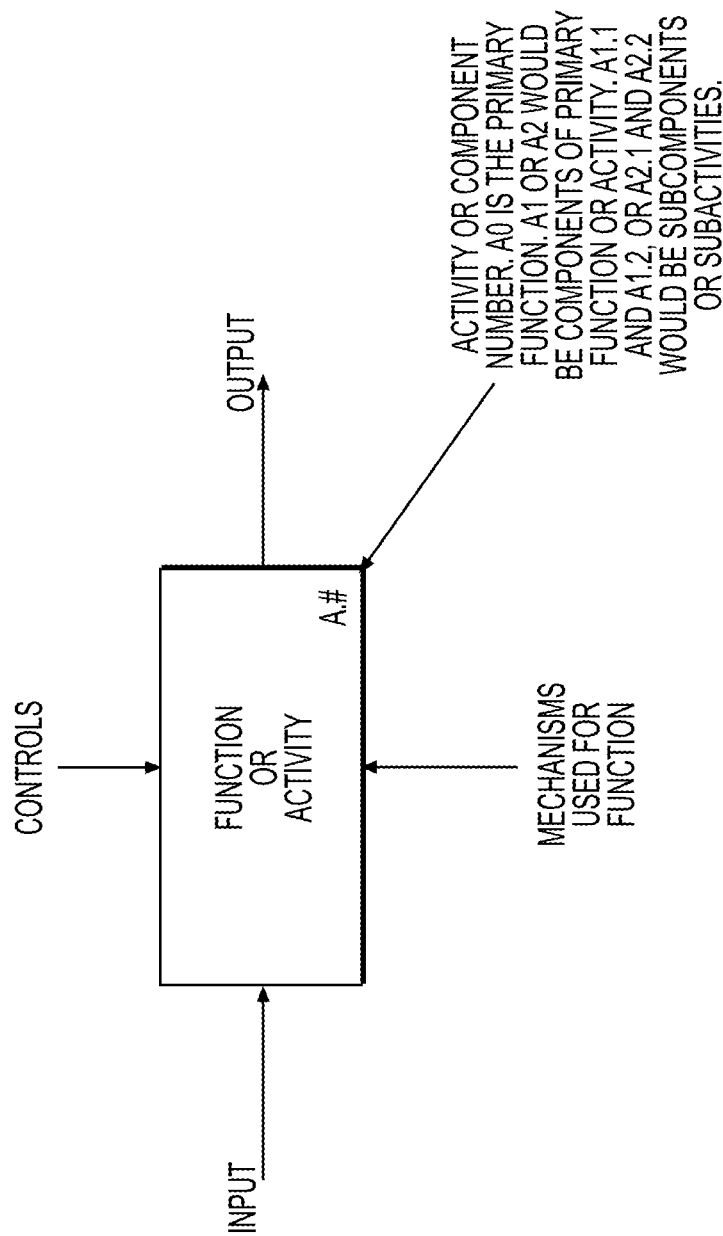
FIG. 2 is a flowchart illustrating a typical function for an Integrated Computer Aided Manufacturing (ICAM) Definition (IDEF) model.

FIG. 2 is an IDEF0 model of the basic system architecture of the imaging system related to the scan. IDEF0 models are used as a functional model for analysis development. IDEF is an acronym for Integrated Computer Aided Manufacturing (ICAM) Definition (IDEF). IDEF0 is the primary function of which all others are either sub-functions or sub-components.

Figure 3:
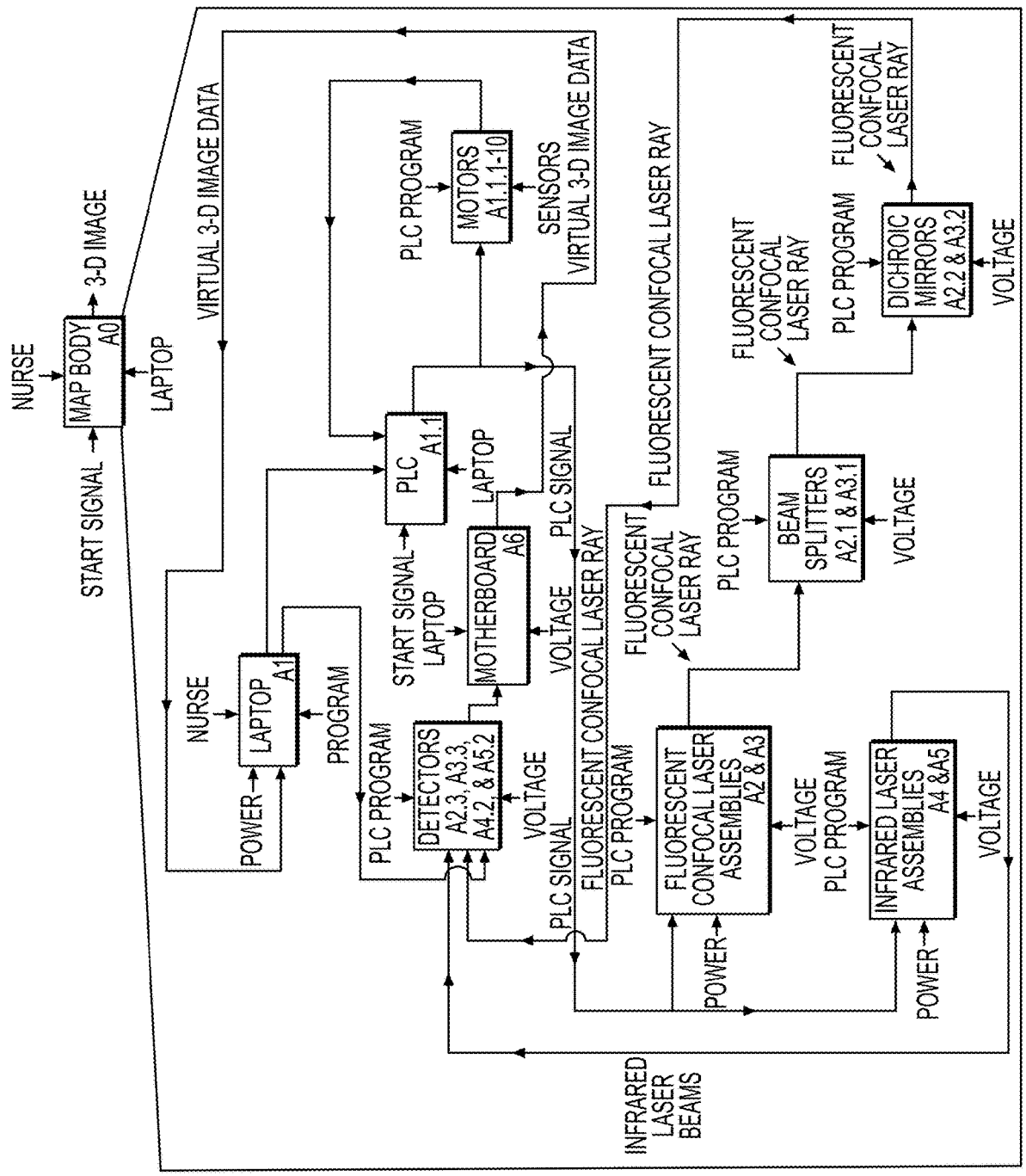
FIG. 3 is a schematic of an IDEF0 model in accordance with one embodiment, wherein the IDEF0 function is the primary function provided by the imaging system, and all other functions in the model are sub-components of the imaging system.

FIG. 3 is an IDEF0 model of the scanning imaging system according to one embodiment. The IDEF0 model portrays how the various components of the imaging system are related to each other in regard to their respective functions. The IDEF0 model shown in the embodiment of FIG. 3 includes Beam Splitters. Beam splitters and X-Y Scanners may be used in certain embodiments. One example of a beam splitter compatible with the imaging system is a dichroic mirror (Chroma catalog #785dcxr-special) mounted on a Nikon TE 300 filter cube (catalog #91001).

In the IDEF0 model shown in FIG. 3, the laptop (A1) under the control of the nurse responds to the nurse's input to start the process, which then in turn prompts the programmable logic controller (PLC-A1.1) to start its internal program which controls the motors of the imaging system. The first action of the PLC (A1.1) is to start the rotation of motor (A1.1.1) that is attached to gearing for a rotatable mount that has all the imaging equipment mounted on it to give rotation of the beams at a level on the patient. Also, in response to any inputs received from the laptop (A1), the PLC (A1.1) provides rotational direction to the servo-motors (A1.1.3 through A1.1.10) of the Fluorescent Confocal Laser Assemblies (A2 and A3), Beam splitters (A2.2 and A3.2), Infrared Laser Assemblies (A4 and A5) to provide beam direction of the Fluorescent Confocal Laser Beams and the Infrared Laser Beams. The PLC also provides rotational direction to the servo-motors of Detectors (A2.3, A3.3, A4.2, and A5.2) to provide the best beam reception. The PLC (A1.1) also provides Laser Assemblies (A2, A3, A4, and A5) laser mode direction provided form laptop (A1). The PLC (A1.1) also provides control the iris opening of the Fluorescent Confocal Laser Assemblies (A2 and A3), plus control of the pinhole openings of the Detectors (A2.3, A3.3, A4.2, and A5.2).

The IDEF0 model shows that when prompted by the PLC (A1.1), the Fluorescent Confocal Laser Assemblies (A2 and A3), plus the Infrared Laser Assemblies (A4 and A5) send forth their laser beams. In respect to Fluorescent Confocal Laser Assemblies and Infrared Laser Assemblies (A2, A3, A4, and A5) the beams pass though Beam Splitters (A2.1, A3.1, A4.1, and A5.1), and then the Beam splitters (A2.2, A3.2, A4.2, and A5.2) before traversing the patient.

The IDEF0 model shows that after the respective beams traverse the patient, the Fourier Transformed beams due to traversing the body of the patient are received by their respective Detectors (A2.3, A3.3, A4.3, and A5.3) on the opposite side of the patient. The beam reception of Detectors (A2.3, A3.3, A4.3, and 5.3) cause analog electrical signals. These analog signals are sent through filters and then on to charge-coupled devices (CCDs) which turn the analog signals to digital signals. These digital signals are then sent on to the Motherboard (A6) of the imaging system which houses the imaging program. The program takes digital signal information and converts that information into virtual 3-D image data. The IDEF0 model shows that the virtual 3-D image data is then sent back to the laptop (A1). This may be done by the CPU program writing the image to a CD-ROM, memory stick or other storage device.

Near the end of each rotation of the rotatable mount, a prompter (dowel) in the rotatable mount causes an electrical impulse to be sent to the PLC (A1.1) to cause the servo-motor (A1.1.2) to move a set rotation creating the next level of the scan, add the number 1 to a count for a digital tachometer in the PLC program, and also causes the PLC to send stored imaging data in the PLC to the CPU storage for program processing, and then wipes the PLC memory to receive the next level's imaging data.

Figure 4:
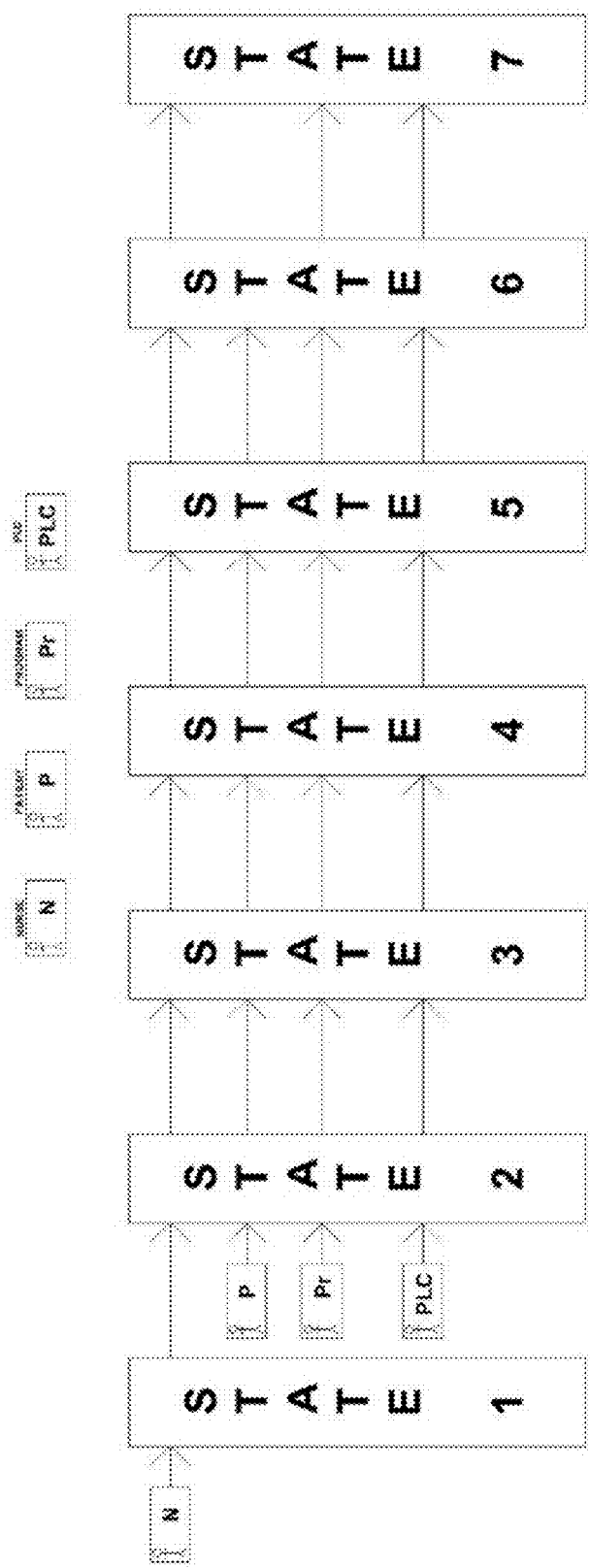
FIG. 4 is a flowchart with an overview of various states of the imaging system and the agents involved at each state in accordance with one embodiment.
Figure 5:
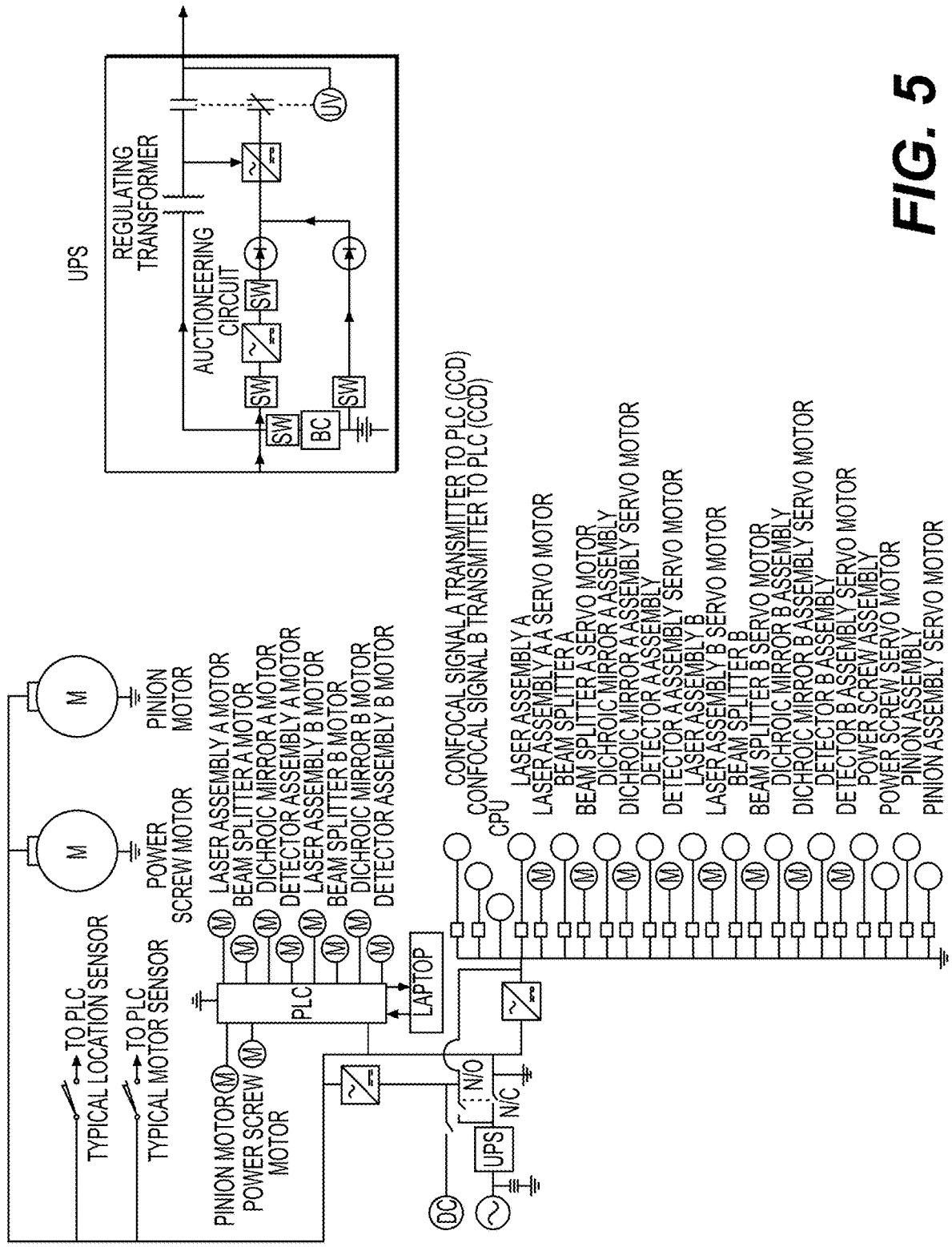
FIG. 5 is an electrical schematic of the imaging system in accordance with one embodiment.

FIG. 4 shows that initially in state 1 the Nurse will be initiating the process in the laptop and inputting the scanning height levels or horizontal positions needed by the physician. In between states 1 and 2 the Patient becomes involved with the process along with the programmable logic controller (PLC) and the scanning program to bring the imaging system to the initial movement state. In between states 1 and 2 the Nurse administers a low concentration of Indocyanine green dye intravenously into the patient, and has the Patient get within the imaging system's scanning space. For indocyanine green dye, the fluence rate should be kept to about 50 mW/cm$^2$ or less to prevent the risk of photobleaching. In between states 2 and 3, the program will become involved ready to receive scanning data, the PLC will start rotation of the imaging head motor causing the imaging system's rotatable mount's rotation, and speed will pick up to the correct rotational scan speed. In between states 3 and 4, the PLC will cause the lasers to activate as well as the scanning levels will begin by incremental rotation of the Stepper Motor causing either change in vertical/horizontal movement caused by rotation of the thread of the Lead (Power) Screw. The physical scanning of the Patient will occur either vertically or horizontally or both, and the program will begin to process the scanning data which will be sent to the program (Pr) memory continuously during the scanning process by having two receiving memories per detector and a toggle to determine which memory is receiving the scanning data from the detector. If the memory for the detector is not receiving scanning data, the PLC will instruct the memory to send its scanning data to the program memory and then to wipe the previous scanning data and be ready to receive new scanning data. At the end of the scan, the PLC will cause the lasers to inactivate, stop rotation of the imaging head motor, and cause the brake to activate. In between states 4 and 5, the PLC will bring the Imaging Head to its maximum either height or horizontal position. The Patient will be removed from the imaging system, the Nurse will remove any IV from the Patient if needed and prompt the imaging system to go to a normal at rest state. In between states 6 and 7 the program will finish processing the scanning data and the write the virtual imaging data to either a memory stick or CD-ROM and then prompt the nurse to retrieve the memory stick or CD-ROM. The physician will either review the virtual image or use the image as a reference image during surgery using the laptop screen.

Figure 6:
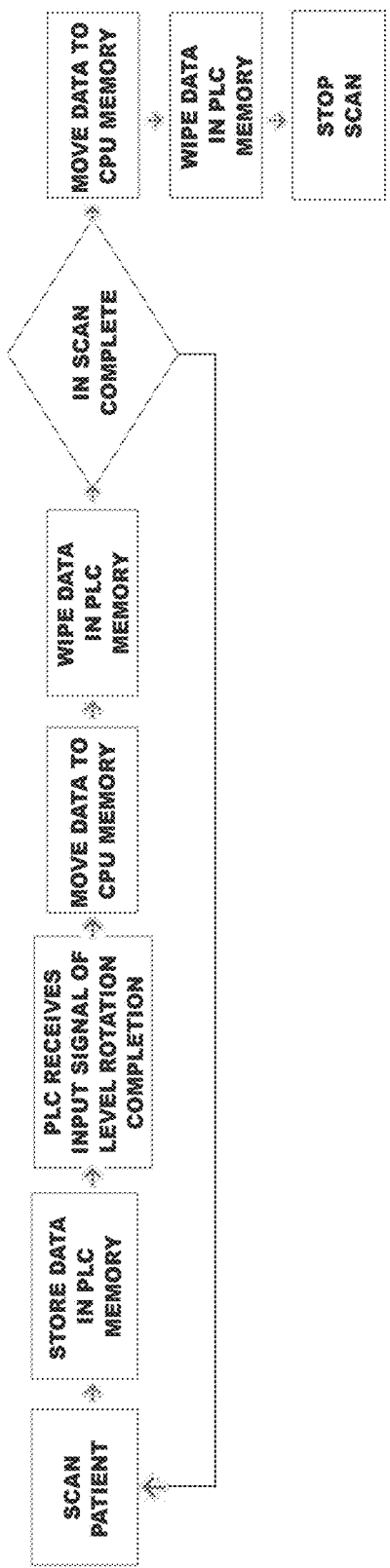
FIG. 6 is a flowchart disclosing one method for generating a three-dimensional image from an imaging system in accordance with one embodiment.
Figure 6:
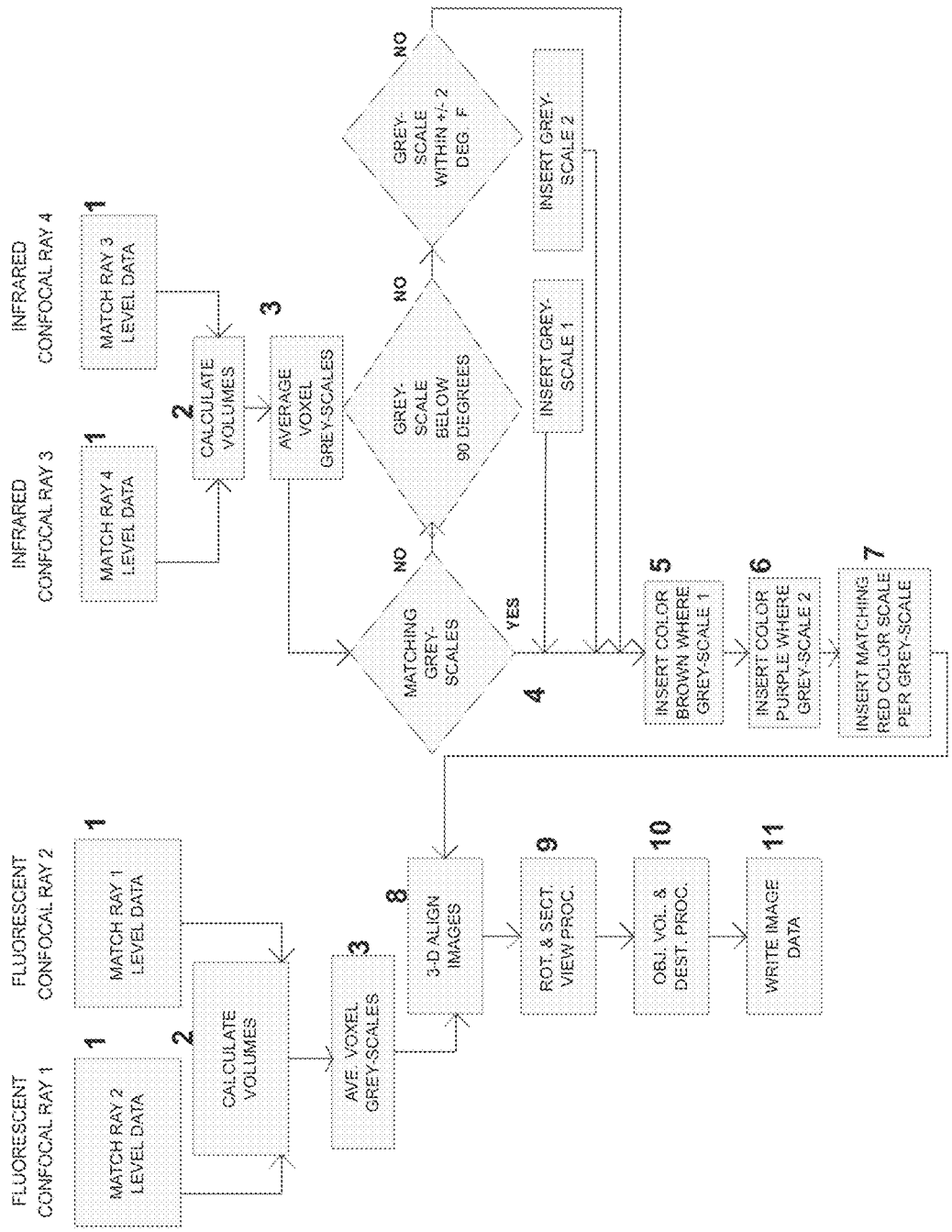

FIG. 6 provides a flow diagram illustrating how images may be generated from data obtained during a scan. Various programs may be used to generate the images, including MATLAB, C++, FORTRAN, and other imaging systems and/or image programs. Step 4 determines if the grey-scale is the same or different than voxels in the vicinity. The program will have a criteria table which determines if the grey-scale is below 90° F. getting grey-scale 1 inserted, or within ±2° F. getting grey-scale 2 inserted. Steps 5 & 6 have voxels with grey-scale 1 get a color brown, and voxels with grey-scale 2 get a purple inserted. The two colors indicate the need for a biopsy. In step 7, The program shall have a light red color scale to be inserted into the other voxels of the infrared/near infrared image per their respective grey-scales. In step 8 the images are aligned, and in steps 9 & 10 the different image rotations and slices are computed. In step 11 the program writes the imaging onto a storage medium such as a CD-ROM or memory stick. The top of the program is the data transfer of the PLC program shown in FIG. 7.

Figure 7:
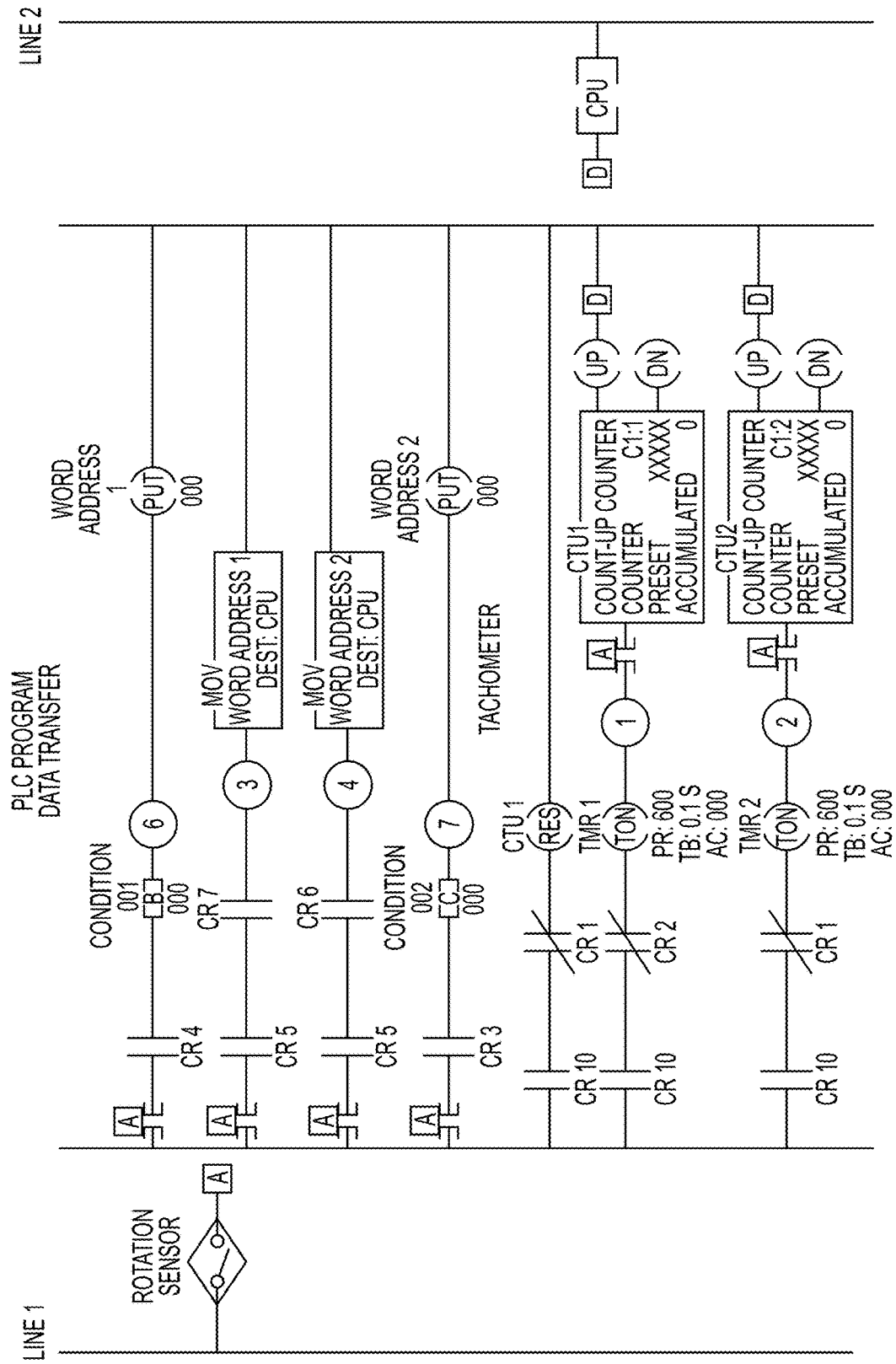
FIG. 7 is a ladder diagram of a program for the programmable logic controller (PLC) in accordance with one embodiment.
Figure 7:
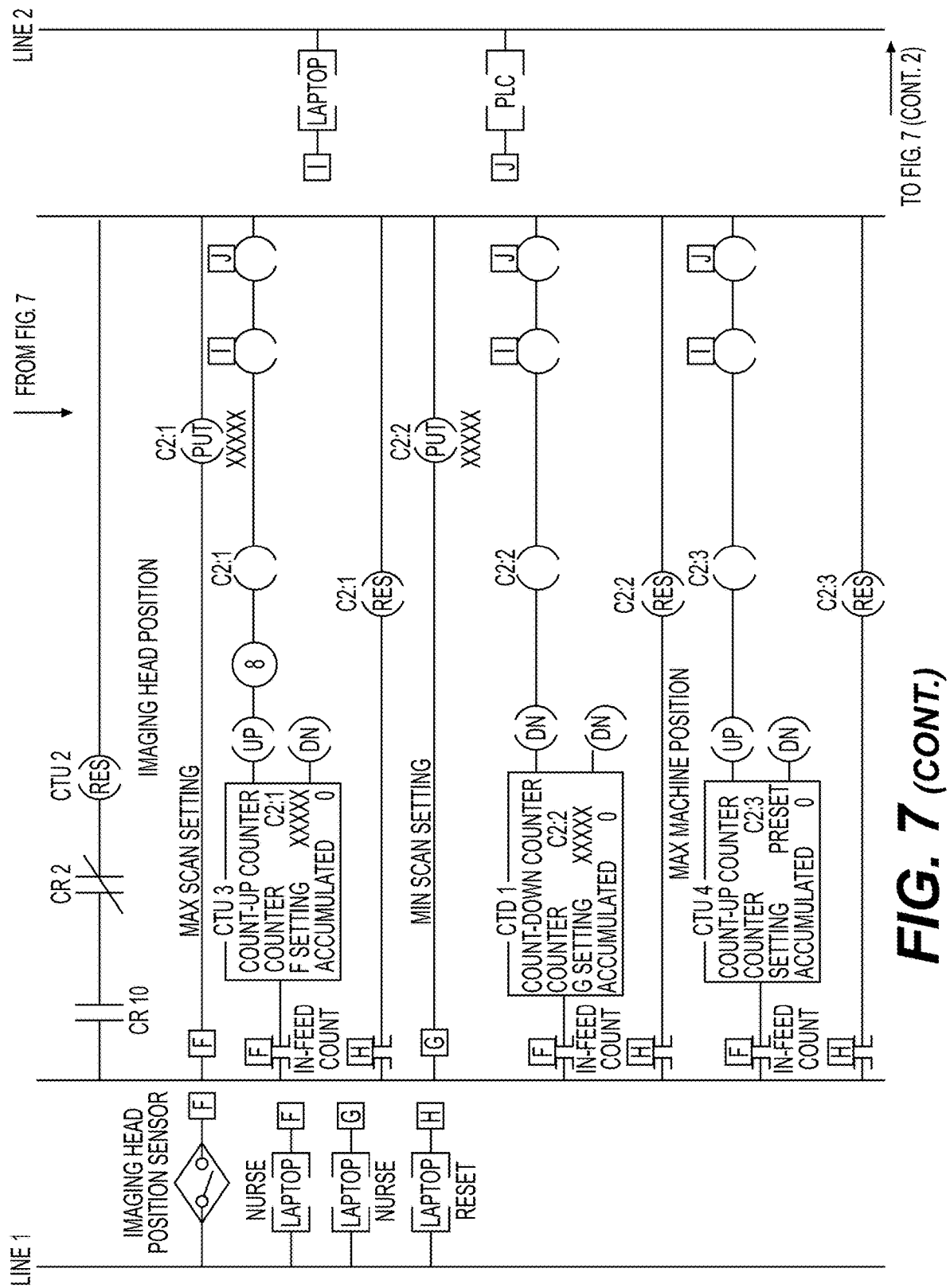

FIG. 7 shows one embodiment of a program adapted to be programmed into the Programmable Logic Controller (PLC) for the imaging system. The program illustrated follows the programming format of the Allen Bradley Corporation PLC programs. Different PLC manufacturers use different program formats but all PLC programs use ladder diagrams like the one shown in FIG. 7. The ladder diagram above follows the states shown in FIGS. 9 through 15. Line 1 shows the inputs into the PLC and line 2 shows the outputs from the PLC. The PLC program selected may depend upon the PLC component chosen for the imaging system.

Figure 8:
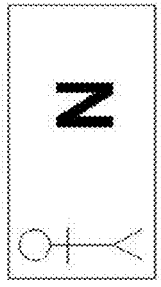
FIG. 8 is a legend for FIGS. 9-15 providing a list of agent codes for various states.

As shown in FIG. 8 and further described by FIGS. 9-15, there may be eleven different human and machine agents involved in producing a virtual 3-D image. These may be: 1) the Nurse, 2) the Patient, 3) the Program, 4) the PLC, 5) the Laptop, 6) the Stepper Motor, 7) the Imaging Head Servo-Motor, 8) the Sensor, 9) the Laser Distance Measurer, 10) the Brake, and 11) the Tachometer. There are other 9V-0.5 A servo-motors involved with the angular positioning of the rays, but they may be involved prior to scanning, concerning the ray position in regards to their respective detection assemblies. Once the angular positions and focus are established by a procedure, the positions and focus are maintained throughout the scanning process and also throughout the stay at a particular site, unless it has been determined that the established positions and focus have been compromised. At that time, the ray positions and focus may be re-established by the procedure. As shown in FIGS. 9-15, there may be seven basic states of the scanning process.

Figure 9:
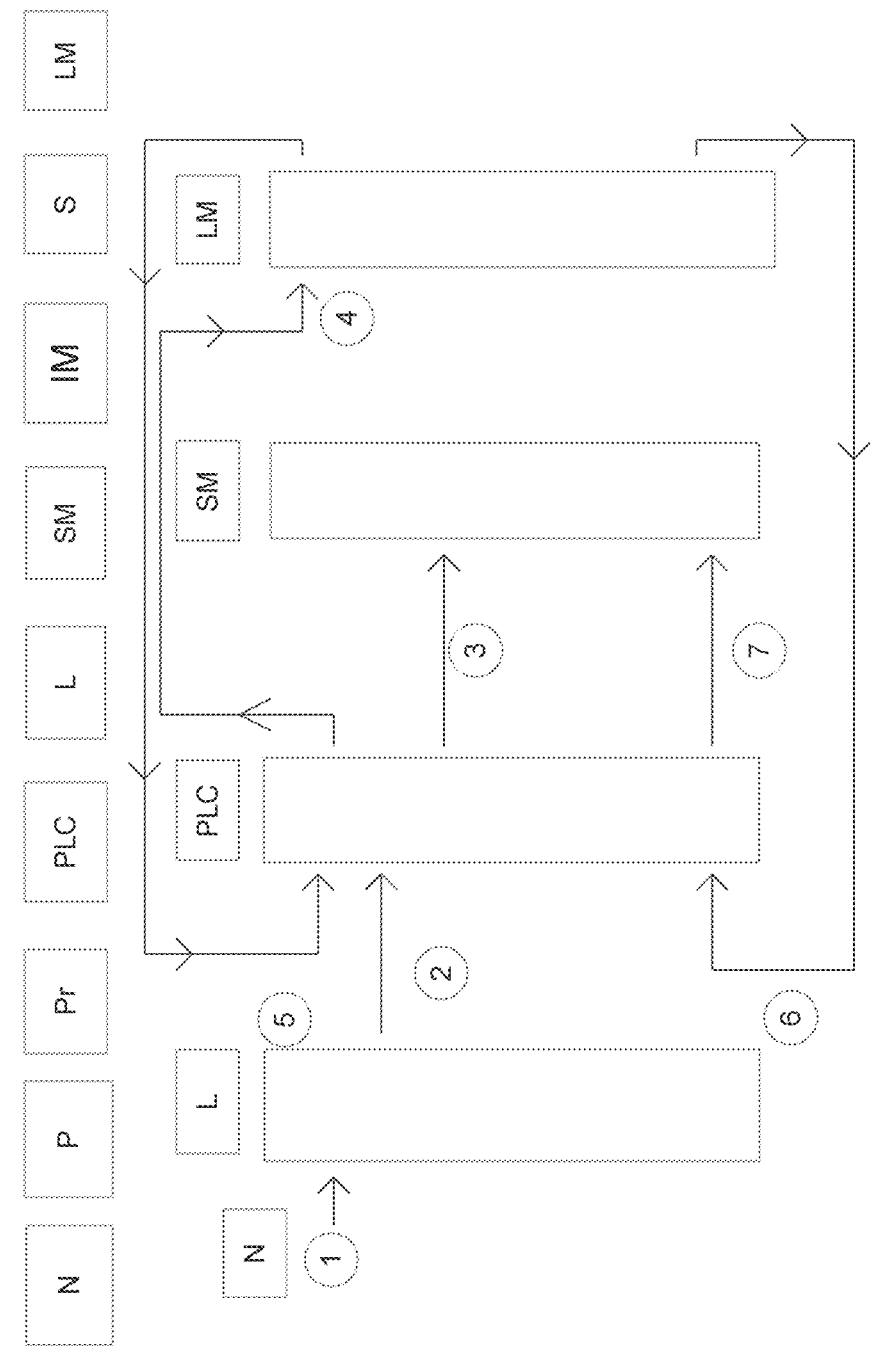
FIG. 9 is a flowchart for State 1 of a scanning process in accordance with one embodiment.

Turning to FIG. 9, a first step in the scanning process is to establish State 1 of the scanning process. It is assumed that the imaging system has been assembled and the procedure to establish ray position and focus have already been performed, the imaging system power is on, the laptop connected to the imaging system, and the program on the laptop is currently running. The Nurse then inputs the designated scan positions into the scanning laptop program. The Nurse then prompts the program to send to the PLC a signal to bring the machine to its maximum machine position. The PLC may then send a signal to the Stepper Motor to rotate continuously to bring the Imaging Head to the maximum machine position. The Stepper Motor responds by rotating continuously sending the Imaging Head toward the maximum machine position. The PLC is constantly checking the Imaging Head distance measurement readings sent to it by the Laser Distance Measurer. Once the PLC receives a reading that corresponds to the maximum machine position, the PLC may send a signal to the Stepper Motor to stop rotating, and the Stepper Motor stops rotation and then the machine is at State 1.

Figure 10:
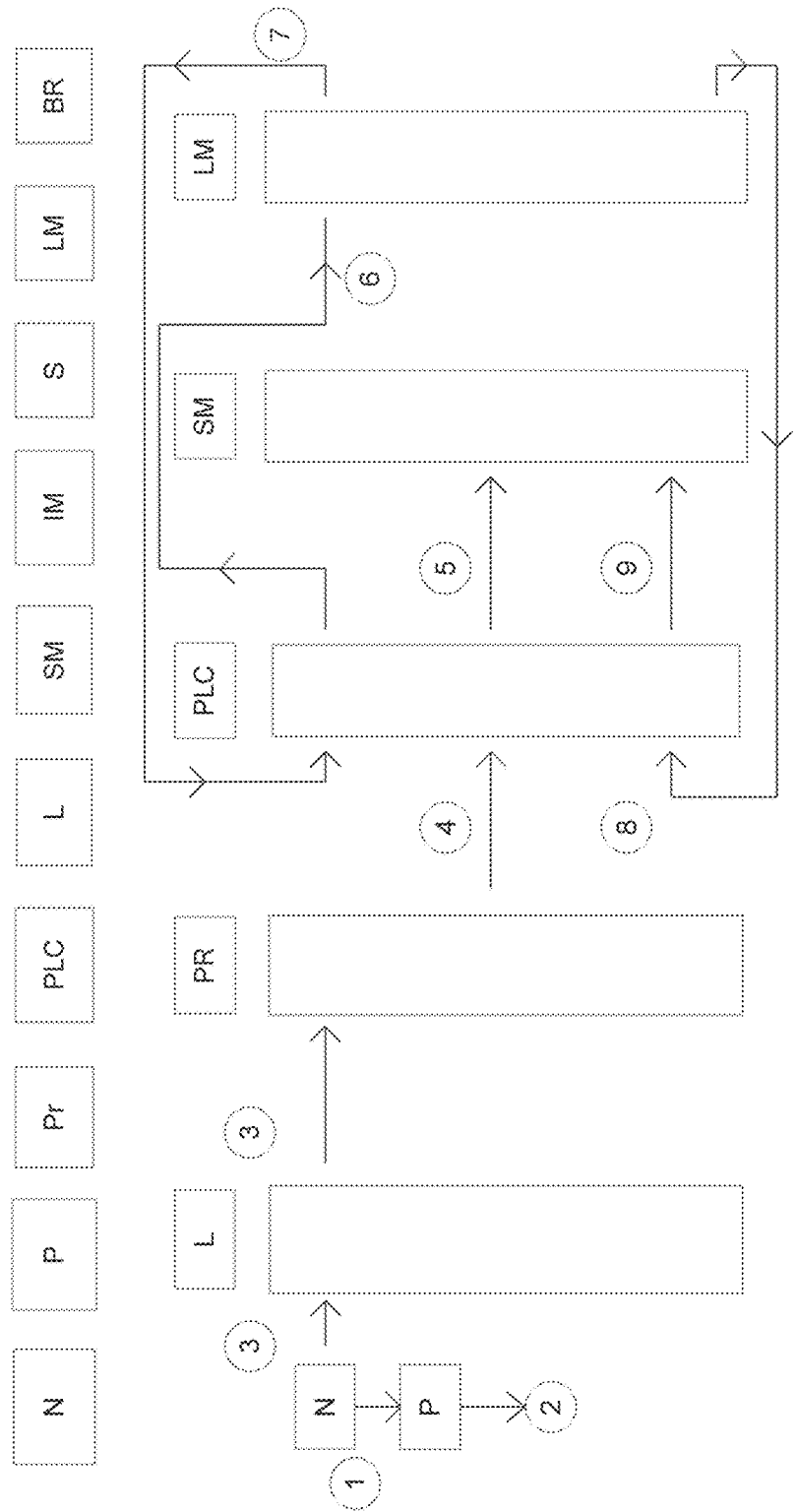
FIG. 10 is a flowchart for States 1 to 2 of a scanning process in accordance with one embodiment.

To establish State 2, a Nurse may administer a non-nuclear imaging medium (low concentration Indocyanine Green Dye, or physician chosen non-nuclear medium) to the Patient (see FIG. 10). The Patient then enters the patient space in the machine. The Nurse activates the scanning Program on the Laptop which also activates the scanning Program within the motherboard. The Laptop Program sends the motherboard Program and the PLC the designated scanning positions, and the Program in the motherboard sends the PLC the signal to start the scan. It should be noted that if there is ever a safety concern at any moment, at a prompt by the nurse, the Program will stop scanning progress at any moment and return the imaging system to State 1, shut the machine off, allowing the patient to depart the machine. The PLC sends a signal to the Stepper Motor to rotate continuously to bring the Imaging Head to the first scan position. The Stepper Motor responds by rotating continuously. Again, the PLC may continuously check the distance readings provided by the Laser Distance Measurer and once the PLC receives a distance reading that corresponds to the initial scanning position, the PLC sends a signal to the Stepper Motor to stop rotation, and the Stepper Motor responds by stopping rotation which brings the imaging system to State 2.

Figure 11:
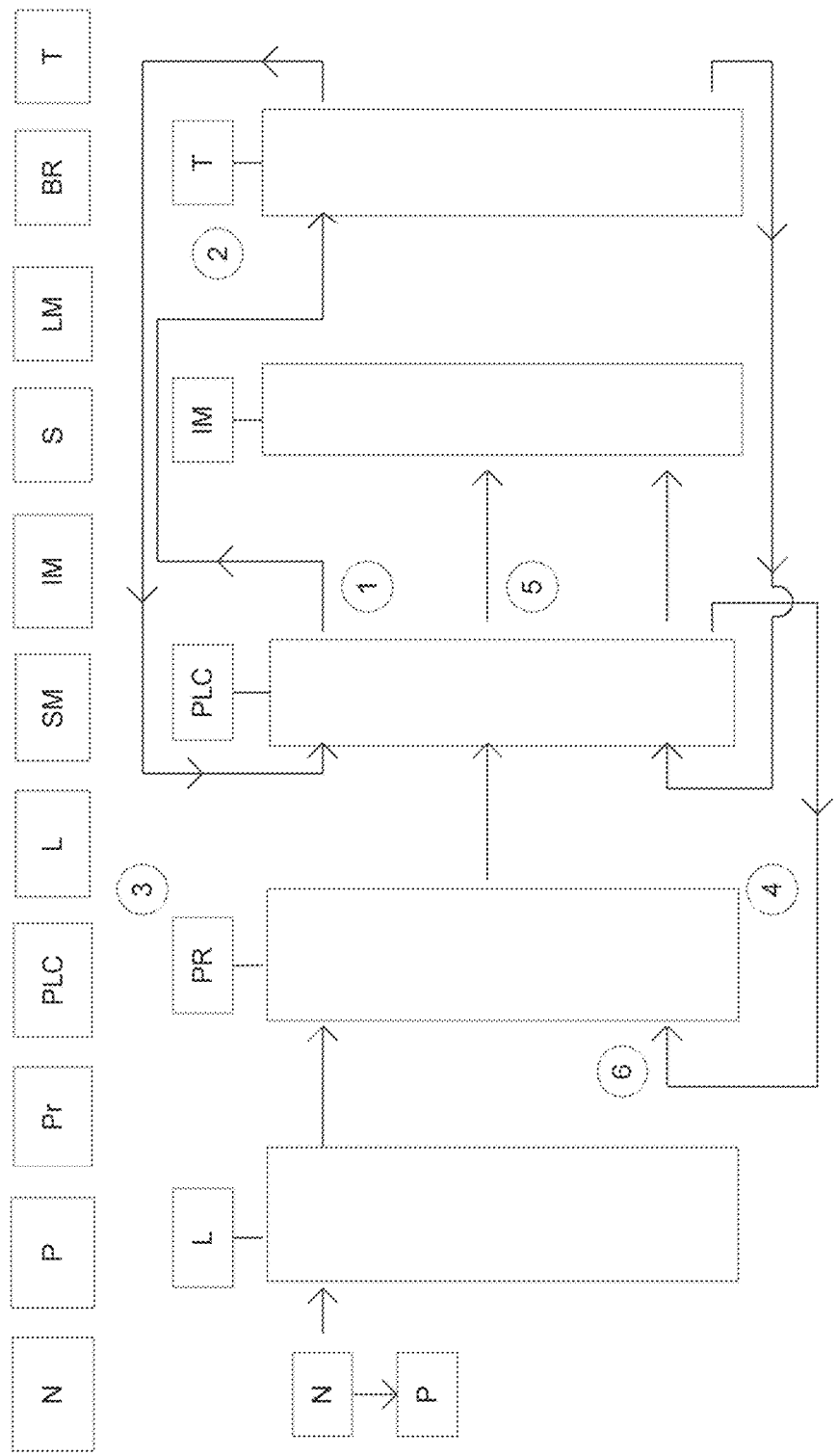
FIG. 11 is a flowchart for States 2 to 3 of a scanning process in accordance with one embodiment.

To establish State 3, the PLC may send a signal to the Imaging Head Servo-Motor to start rotation, and the Imaging Head Servo-Motor responds by starting rotation (see FIG. 11). The PLC then sends a signal to the Imaging Head Servo-Motor to increase speed until normal scanning rotational speed is reached. The PLC continuously receives tachometer readings from the Tachometer and when the PLC receives a tachometer reading that corresponds to normal scanning rotational speeds, the PLC then sends a signal to the Imaging Head Servo-Motor to maintain rotational speed. The PLC then sends a signal to the Program that the machine is ready to scan, and the machine is now at State 3.

Figure 12:
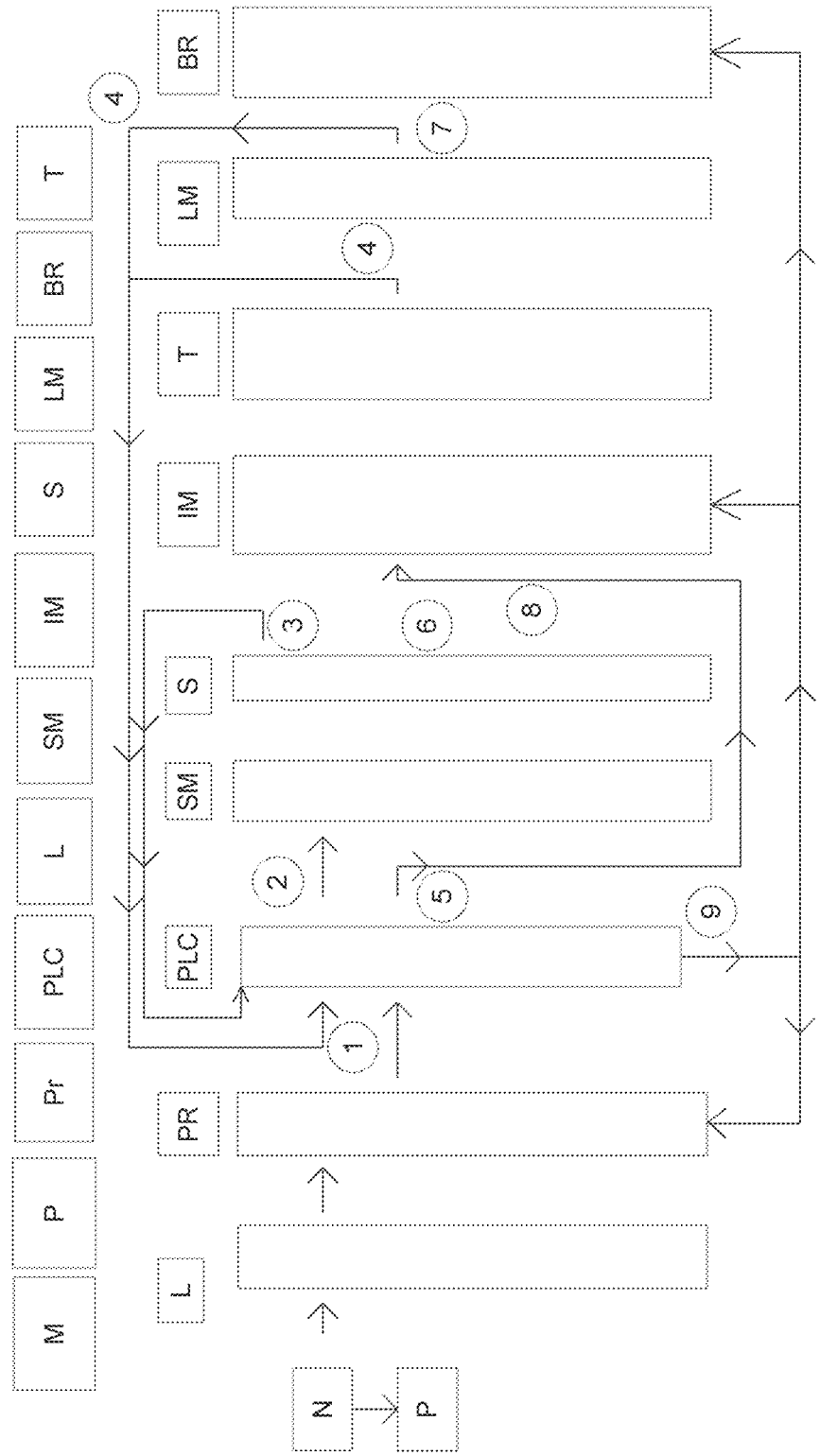
FIG. 12 is a flowchart for States 3 to 4 of a scanning process in accordance with one embodiment.

To establish State 4, the Program may send a signal to the PLC to start the scan (see FIG. 12). The PLC then activates all lasers and sends a signal to the Stepper Motor to step rotate 1 position and await a sensor signal to the PLC that the Imaging Head is in the first scan position, and PLC then begins to start receiving scan data from the CCDs. The PLC is continuously receiving tachometer readings from the Tachometer and issuing commands to either raise or lower rotational speed to maintain proper scanning rotational speed. The PLC may also be continuously receiving distance readings from the Laser Distance Measurer concerning Imaging Head position. The incremental scan process is for the PLC to receive a signal from the sensor that faces the rotating ring of the Imaging Head that it is within a certain position from the end of the rotation for the scanning level, and the PLC sends another signal to the Stepper Motor to rotate 1 position to move the Imaging Head incrementally toward the final scan position. The Stepper Motor may respond by rotating 1 position and the PLC switches the internal memory receiving scanning data from the CCDs, sends the scanning data just received data to the motherboard memory, wipes the scanning data just sent from the internal memory that just sent and awaits the next sensor signal. During all this action, the Program in the motherboard may be beginning to process data and starts to construct Fluorescent Confocal Microscopy and Infrared Microscopy Images. Once the PLC receives a distance reading from the Laser Distance Measurer that the Imaging Head has reached the maximum designated scanning position, the PLC awaits the next rotating ring sensor signal. Once the next Sensor signal is received by the PLC, the PLC inactivates all lasers and sends a signal to the Imaging Head Servo-Motor to stop rotation, and the Imaging Head Servo-Motor stops rotating. The PLC may then send a signal to the Brake to engage which then engages, and once the PLC receives a zero reading from the Tachometer the PLC sends a signal to the Brake to disengage and the Brake responds. The PLC sends the final data set from its internal memory to the motherboard memory and wipes the PLC memory. The PLC may then send a signal to the Program that the scan is complete and the imaging system is now at State 4.

Figure 13:
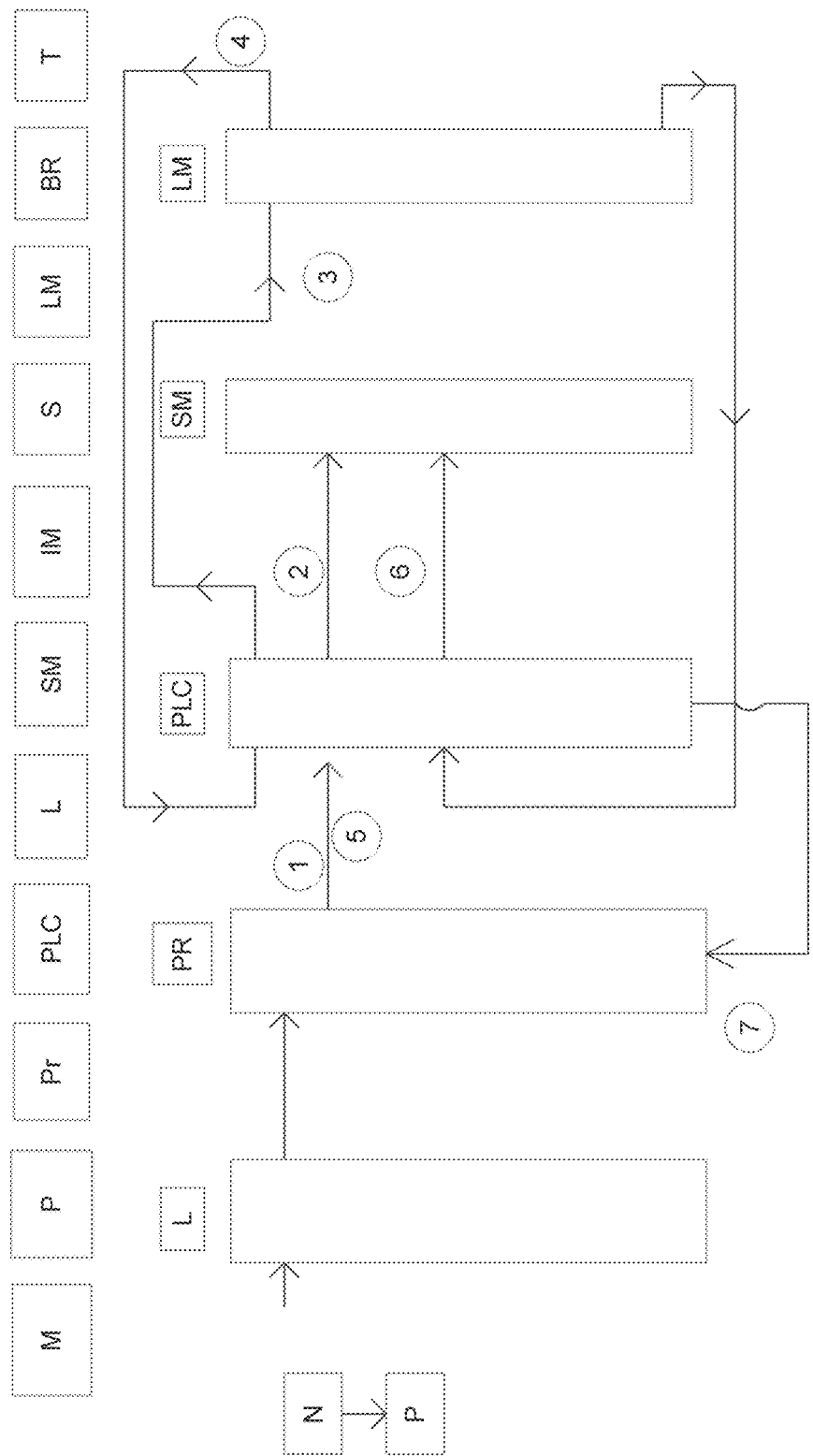
FIG. 13 is a flowchart for States 4 to 5 of a scanning process in accordance with one embodiment.

To establish State 5, the Program may send a signal to the PLC to stop the scan and go to maximum machine position (see FIG. 13). The PLC sends a signal to the Stepper Motor to rotate in the opposite direction continuously to bring the Imaging Head to the maximum machine position. The PLC checks the distance readings from the Laser Distance Measurer and when the reading shows that the Imaging Head is at maximum machine position, the PLC sends a signal to the Stepper Motor to stop rotation and the Stepper Motor responds. The PLC then sends a signal to the Program that the machine is at maximum machine position and the imaging system is now at State 5.

Figure 14:
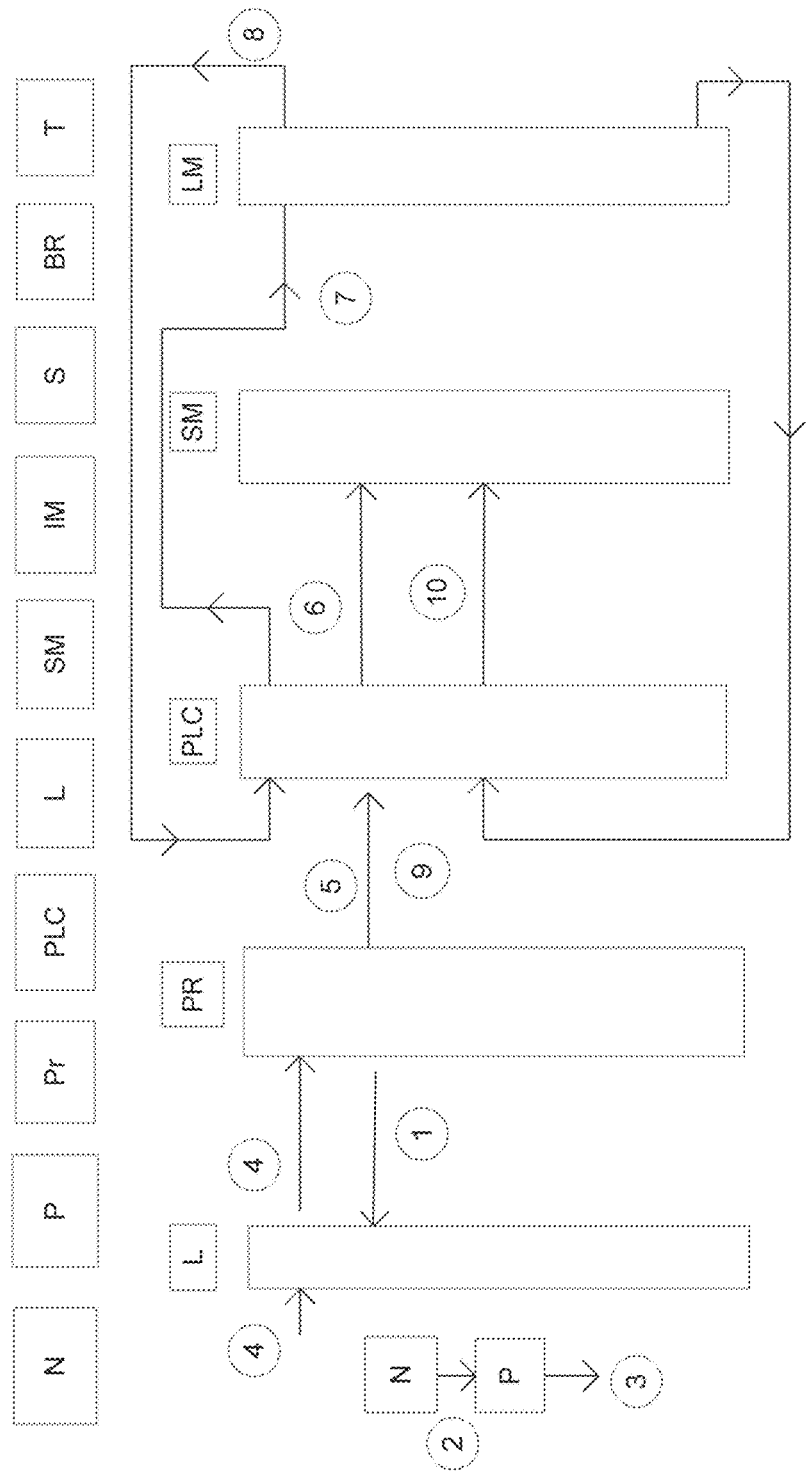
FIG. 14 is a flowchart for States 5 to 6 of a scanning process in accordance with one embodiment.

To establish State 6, the motherboard Program then may send a signal to the Laptop Program that the scan is complete, and the Imaging head is at maximum machine position (see FIG. 14). A Nurse may instruct the Patient to depart the machine, if an IV was used throughout the scanning process, the IV may be removed from the Patient. The Nurse may prompt the Program to continue processing the 3-D image and send the imaging system to an At Rest position. The PLC sends a signal to the Stepper Motor to rotate continuously in the direction that brings the imaging system to the At Rest position. The PLC may continuously monitor the readings from the Laser Distance Measurer for a reading that corresponds to an At Rest machine position. Once the PLC receives a reading that corresponds to the At Rest machine position, the PLC may send a signal to the Stepper Motor to stop rotation in the counter-clockwise position, and the stepper Motor stops rotation bringing the imaging system to State 6.

Figure 15:
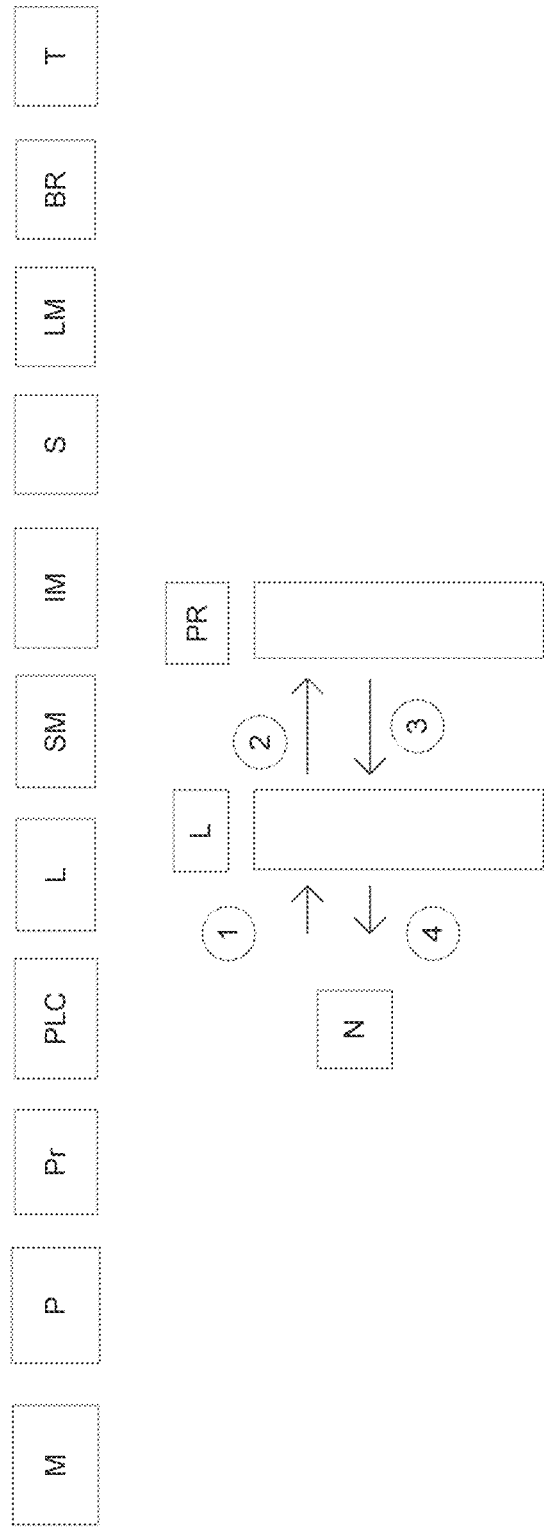
FIG. 15 is a flowchart for States 6 to 7 of a scanning process in accordance with one embodiment.

To establish State 7, the Nurse may prompt the program in the Laptop to send a signal to the Program in the motherboard to complete the 3-D image (see FIG. 15). Laptop Program may send a signal to the motherboard Program to complete 3-D image. Motherboard Program may complete the 3-D image and sends signal to Laptop Program that 3-D image is complete. A Nurse may then insert a storage medium such as a CD-ROM or memory stick into the Laptop or CD-ROM receptacle/USB port of motherboard, and prompt the motherboard Program may then write the 3-D image to the storage medium, and then the Nurse may remove the storage medium for later use. A Motherboard may keep the 3-D image in associated coupled memory until instructed to delete image. The machine is now at State 7.

Figure 16:
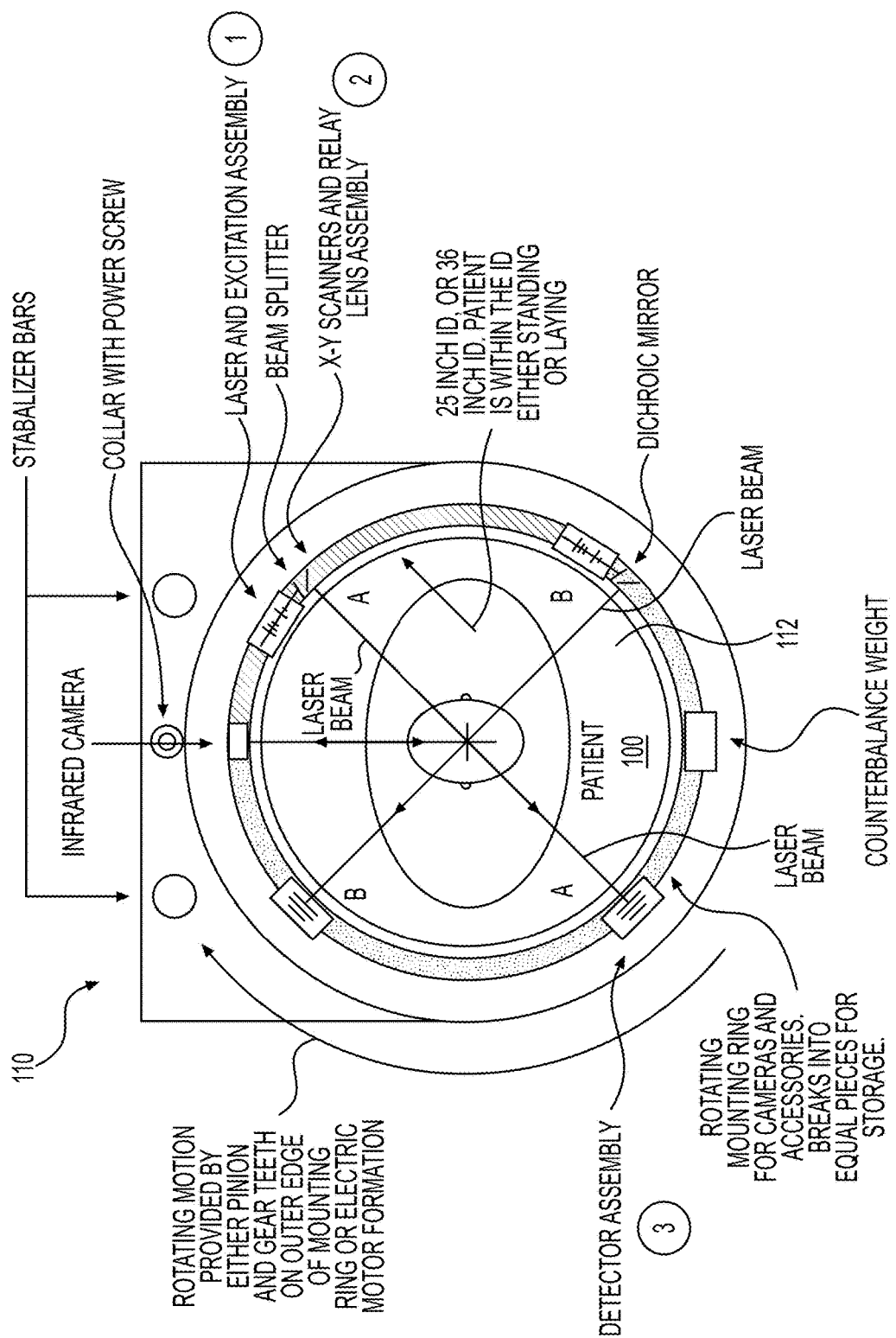
FIG. 16 is an overhead view of one embodiment of an imaging system with a subject within a patient space.

FIG. 16 provides an overview of the imaging system 110 in operation. A patient 100 is positioned within the patient space 112. During operation, the imaging system 110 rotates along an x-z axis to obtain cross-sectional data, and traverses along a longitudinal y-axis to obtain three-dimensional data for generating voxels as described in FIG. 6.

Figure 17:
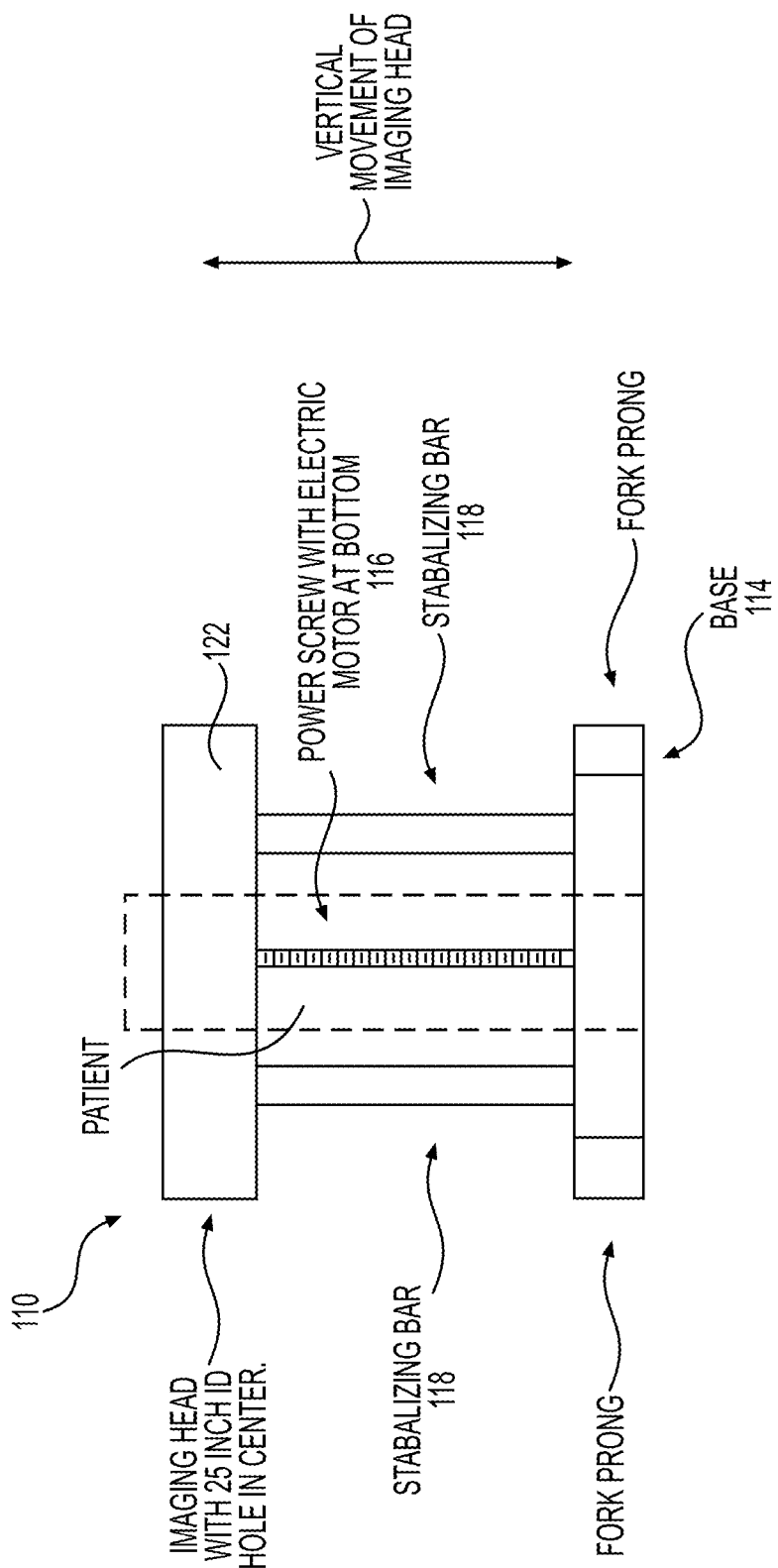
FIG. 17 is a front elevational view of one embodiment of an imaging system wherein the longitudinal axis is vertical.
Figure 19:
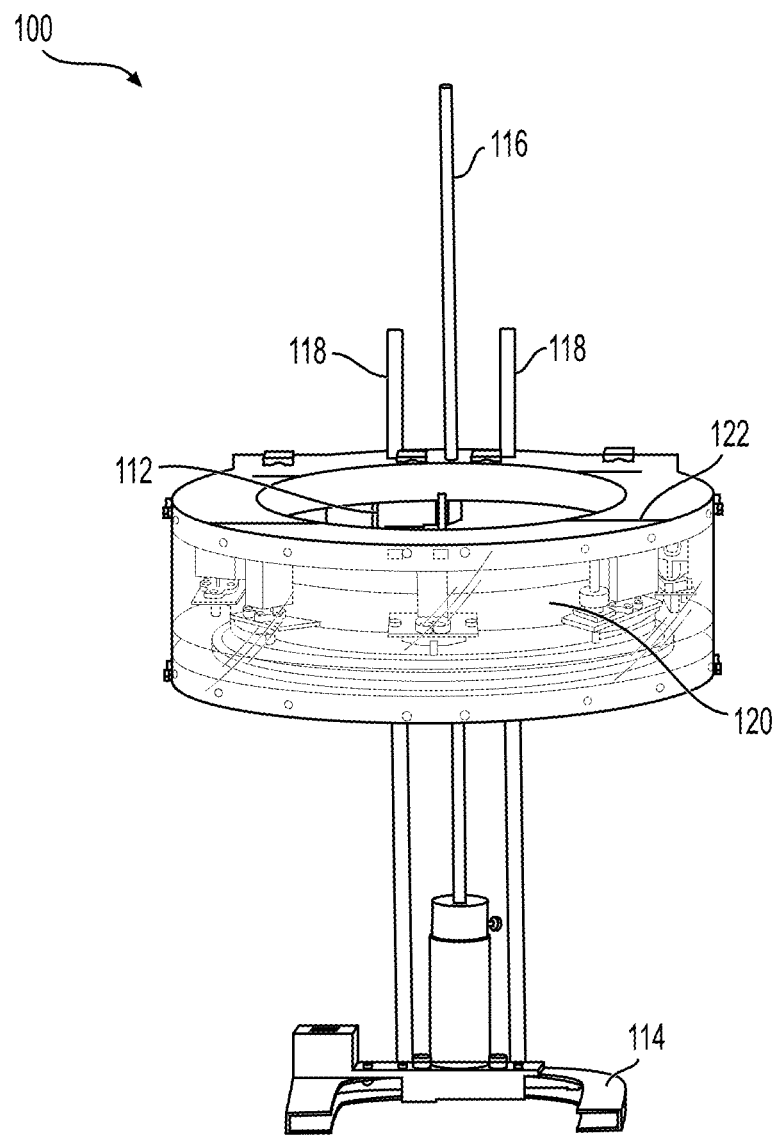
FIG. 19 is a front perspective view of a vertical imaging system in accordance with one embodiment.

FIGS. 17 and 19 illustrate one embodiment of an imaging system 110 having a vertical model structure. In FIG. 17, the structure on the left hand side of the base 114 is the housing for the uninterruptable power supply (UPS). The main structure at the base is the housing for a stepper motor. On top of that structure is the Lead (Power) Screw 116 with stabilizing bars 118 on either side of the Lead Screw 116 with which the rotatable mount and Rotatable Mount Housing 122 travel vertically up and down.

Figure 18:
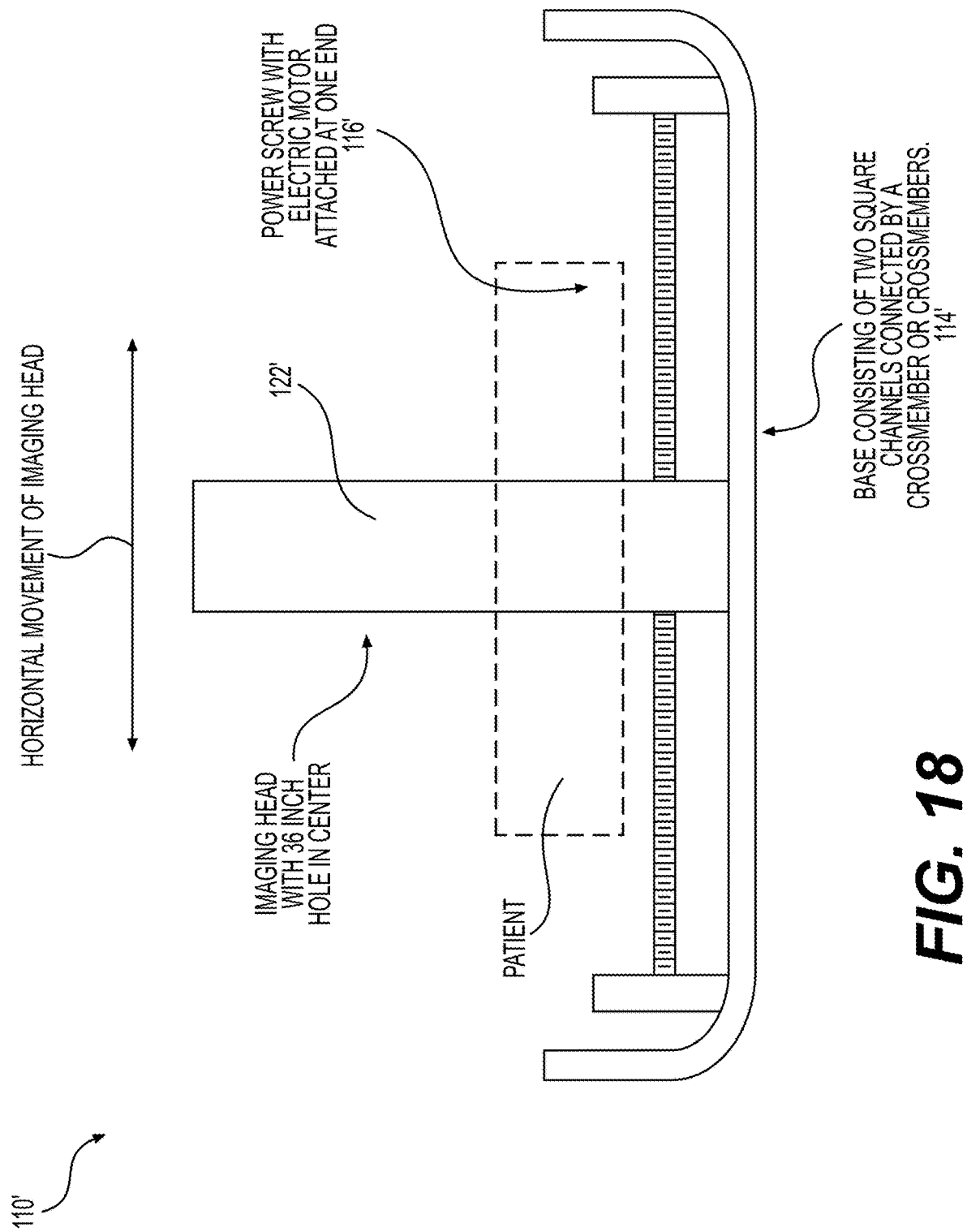
FIG. 18 is a front elevational view of one embodiment of an imaging system wherein the longitudinal axis is horizontal.
Figure 20:
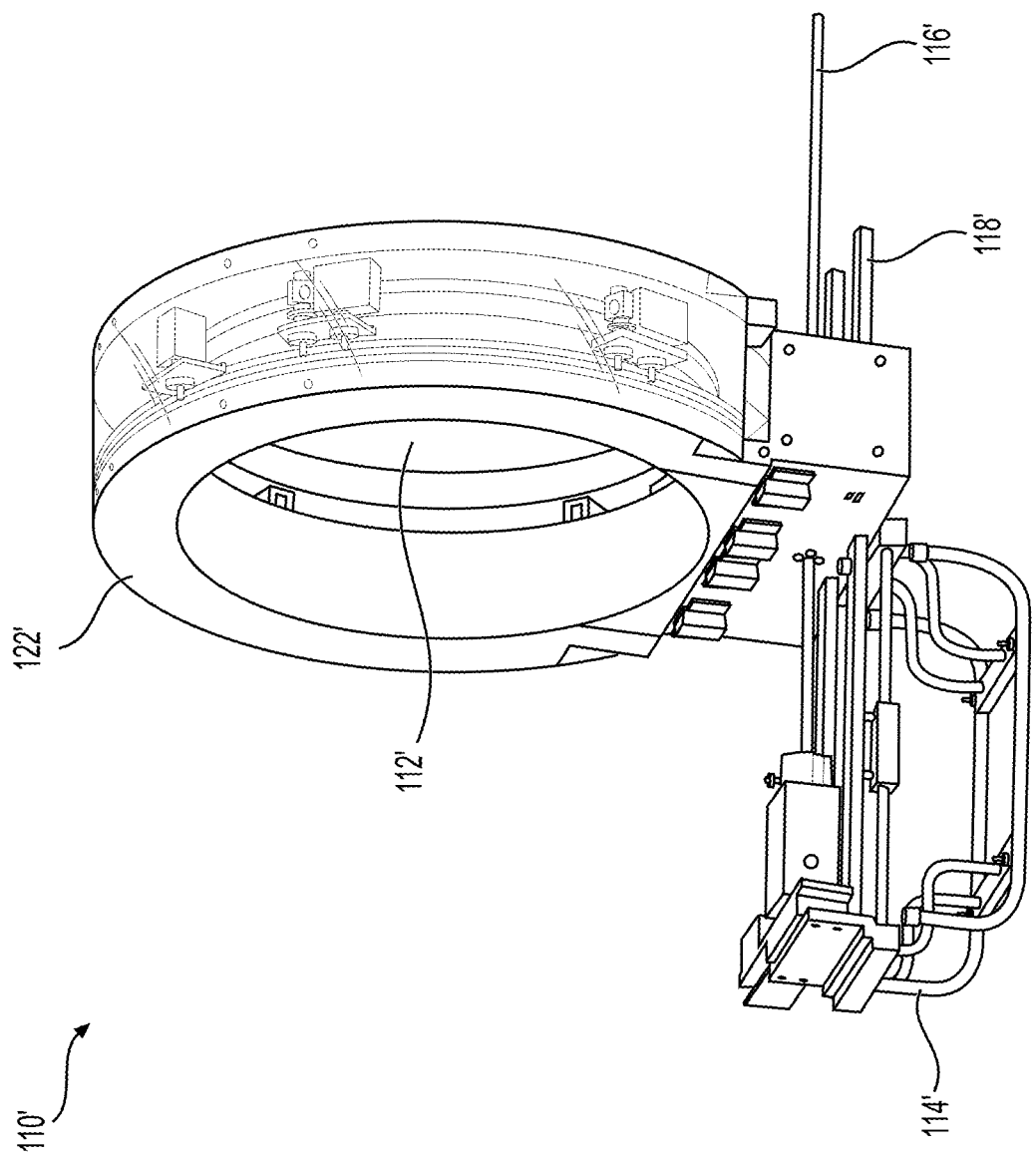
FIG. 20 is a front perspective view of a horizontal imaging system in accordance with one embodiment.

FIGS. 18 and 20 illustrate one embodiment of an imaging system 110' having a horizontal model structure. FIG. 18 shows that the travel configuration of imaging system 110' is horizontal. In both horizontal and vertical configurations, the confocal parts circulate around the subject. The basic configuration is similar, but not totally identical. The horizontal imaging system 110' includes a base 114' comprising two channels connected by one or more crossmembers. The rotatable mount housing 122' is attached to a lead screw 116'. The same imaging head may be used in both models.

Figure 21:
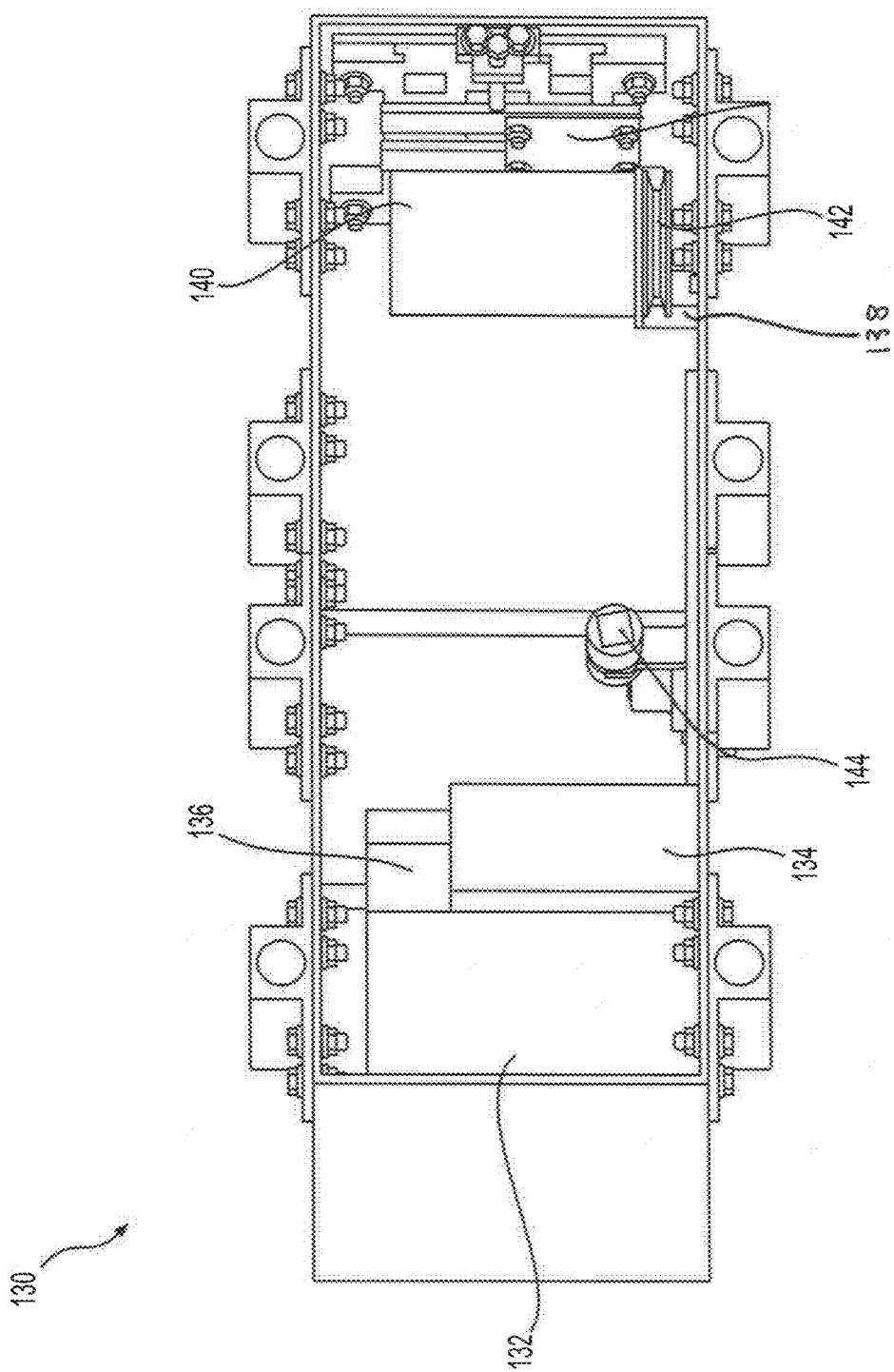
FIG. 21 is a front perspective view of an imaging head in accordance with one embodiment.

FIG. 21 shows one embodiment of an imaging head 130. The imaging head 130 may be adapted for use with both vertical imaging system 110 and the horizontal imaging system 110', wherein both imaging heads 130 may be identical. The Imaging Head 130 includes a CPU 132 where the imaging program is held, a programmable logic controller PLC 134, and a wireless slip-ring 136. Each component may have either an internal wireless antenna or a mounted wireless antenna and communicates with the PLC via the wireless slip-ring. Small components, such as confocal lasers may have a battery that can be changed out for some power, but small motors, confocal components, and brake can also have a small amount power transmitted via the wireless slip-ring 136. A brake 138 is further included to lower the rotational speed of the imaging elements, and the electric motor 140 that provides rotation to the Rotatable mount 120 is hard wired but receives commands via the wireless slip-ring 136. At the bottom of the electric motor's shaft is shown a sheave 142 to provide rotation to a V-belt. Other embodiments may also use a pinion and gear for rotation. At the right of the electric motor 140 is shown its mounting that allows for tightness adjustment of the V-belt. In the lower middle of the picture is shown a proximity sensor 144 to sense the presence of the previously discussed dowel indicating the end of each rotation of the Rotatable mount 120 causing transfer of data to the CPU 132, wiping the PLC data, and shifting the position of the imaging head 130. Behind the sensor is shown the collar for the Lead Screw.

Figure 22:
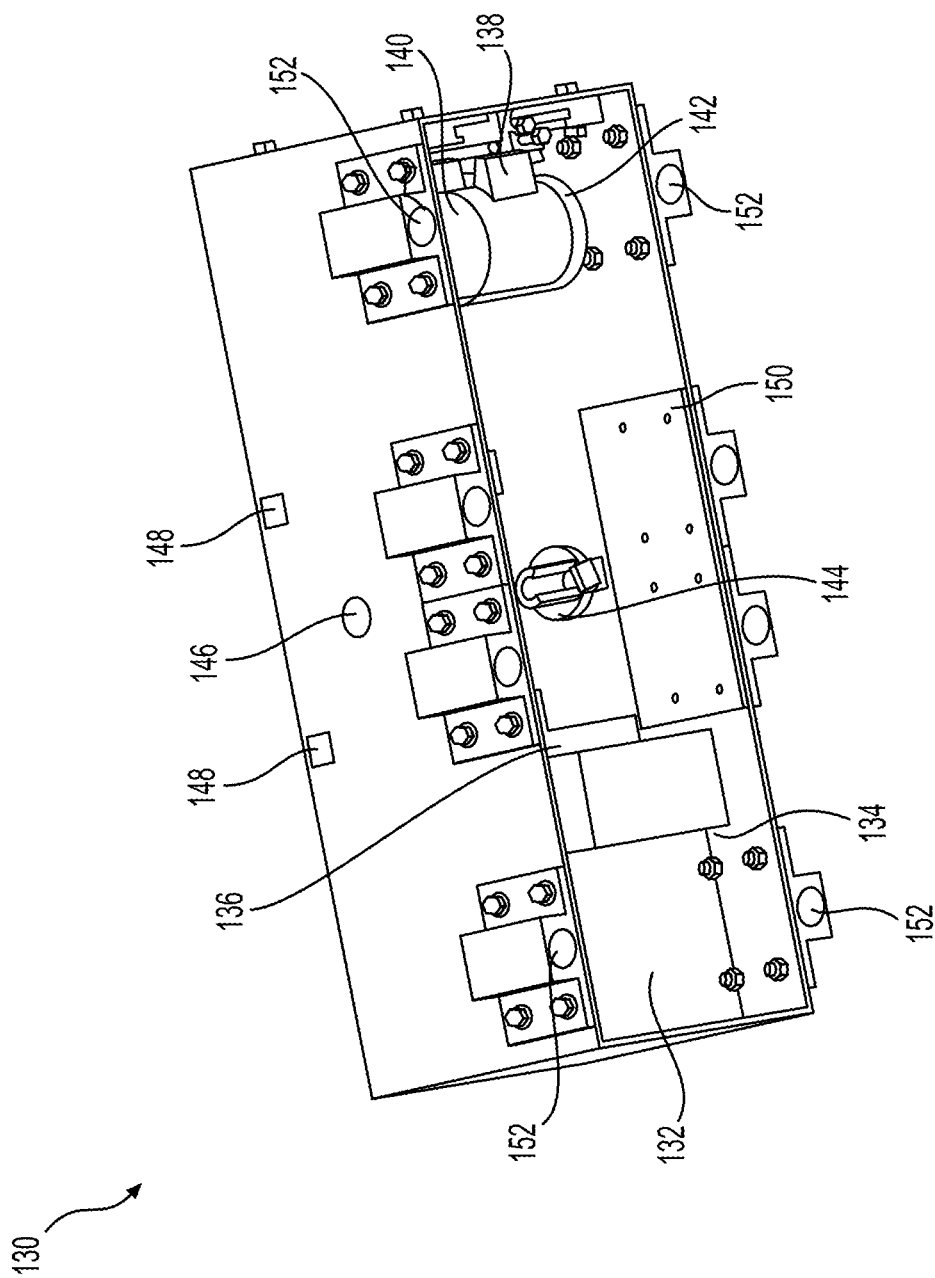
FIG. 22 is a top perspective view of the imaging head in FIG. 21.

FIG. 22 shows the hole 146 in the top of the imaging head 130 that allows the Lead Screw to pass through and also shows the holes 148 for the stabilizing rods to pass through. Each of the holes 148 for the stabilizing rods have associated ribs in the housing that totally surround the rods. The center bottom shows a bearing plate 150 for the rotatable mount to slide on while inside the Imaging Head. The eight holes 152 shown are for the prongs of the Rotatable Mount Housing Connector to engage with.

Figure 23:
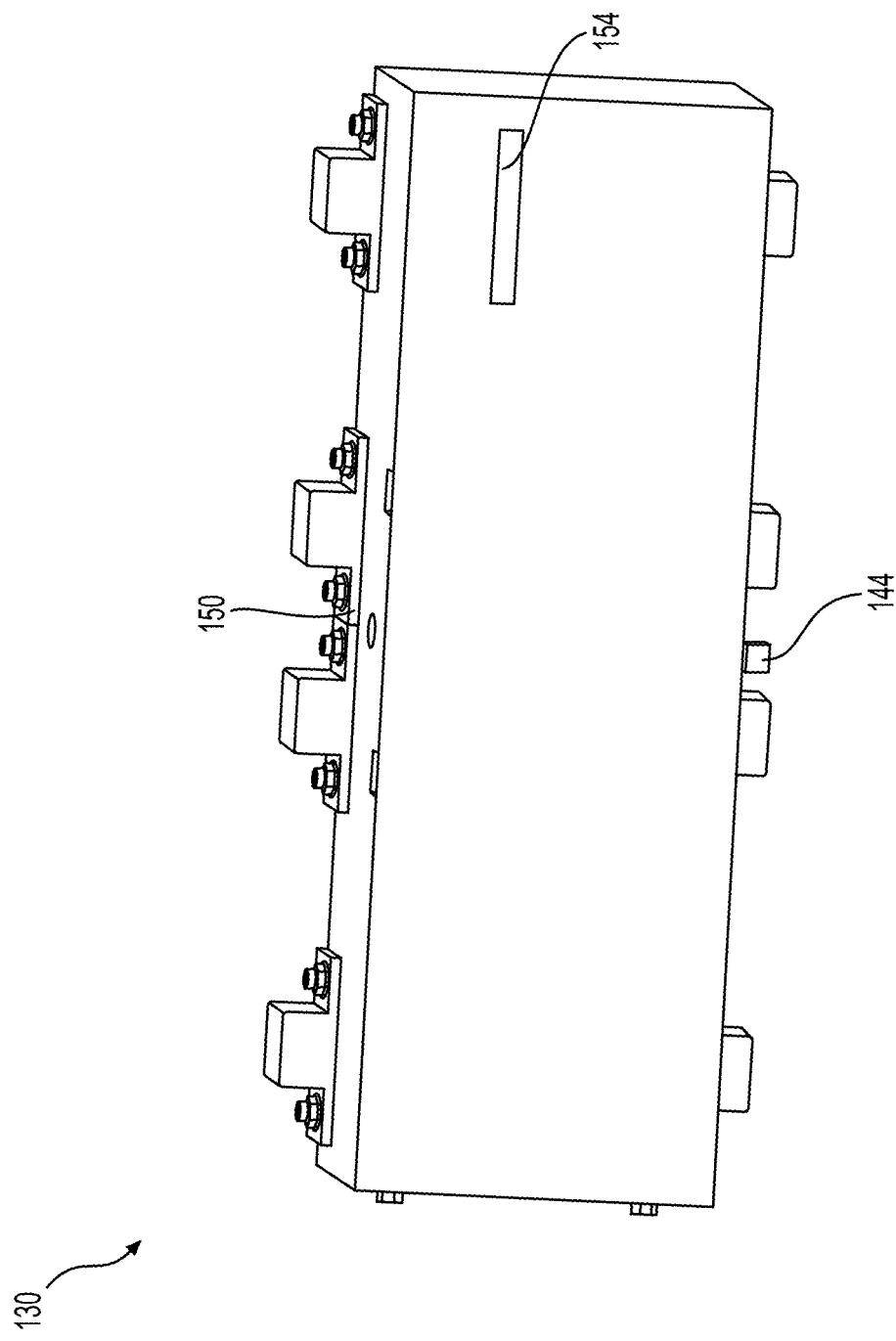
FIG. 23 is a rear perspective view of the imaging head in FIG. 21.

At the center-bottom of FIG. 23 is shown a proximity sensor 144 which is a laser distance measurer hat indicates the position of the imaging head 130 in relation to the position of the Stepper Motor. A slot may be included on the imaging head 130 to insert a CD-ROM disc, memory stick or other storage device to write the images on.

Figure 24:
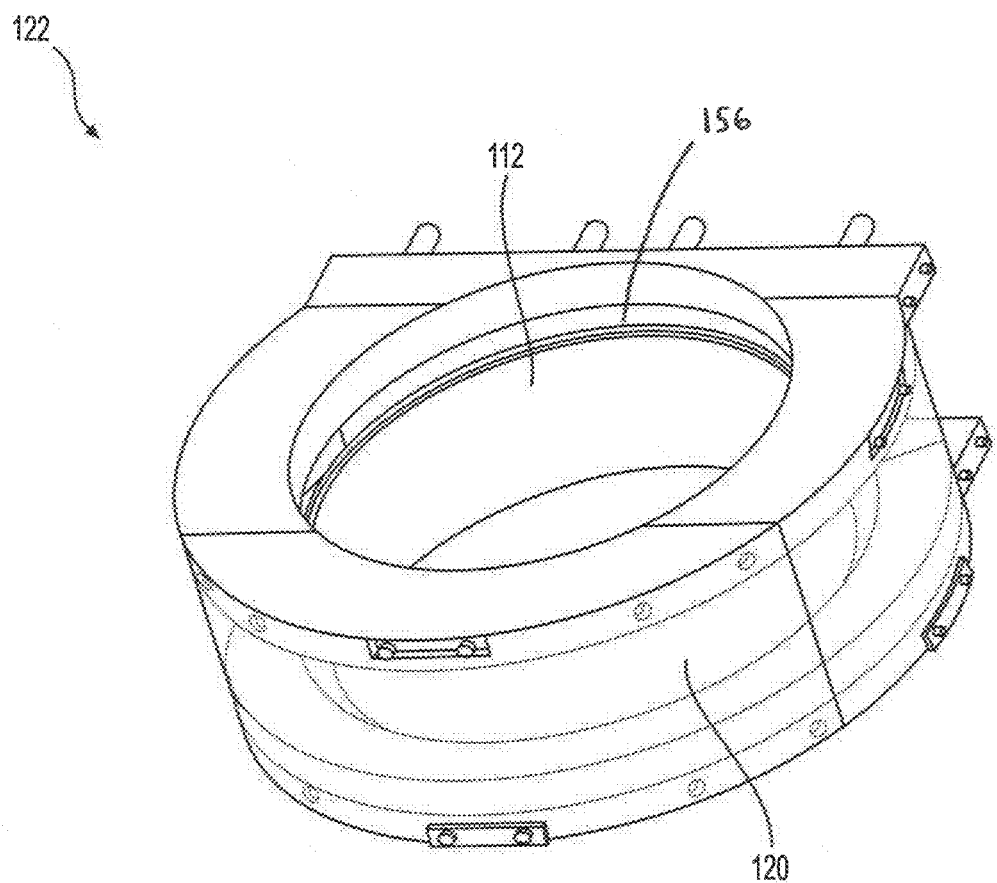
FIG. 24 is an overhead perspective view of a rotatable mount housing in accordance with one embodiment.

FIG. 24 shows that there is a window 156 in the housing 122 for the rays to pass through and also shows the plastic shields to protect the public from flying objects in case there is a failure of parts. The housing 122 may be segmented and connected by screws. Each segment of the public shield 120 has a portion of the annular ring which holds the rotatable mount 120 in place to prevent upward free-travel of the rotatable mount 120.

Figure 25:
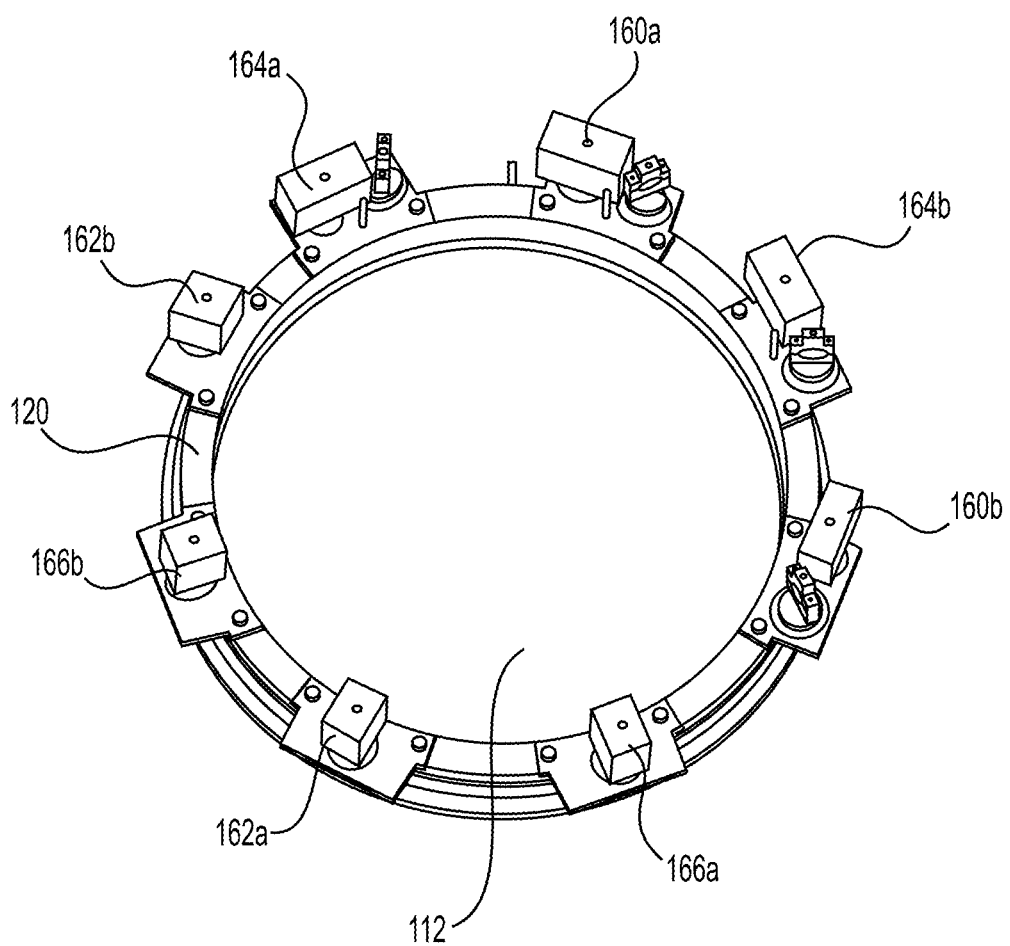
FIG. 25 is a top perspective view of a rotatable mount having its confocal fluorescent microscopy assemblies and thermographic assemblies arranged in accordance with one embodiment.

FIG. 25 shows the first and second fluorescent confocal assemblies, 160a and 160b, which have both the Laser Excitation Assemblies and a Beam splitter. One example of a fluorescence excitation light compatible with the imaging system is a model A-240-D (Dolan-Jenner) dual 150 W halogen source. About 180 degrees from the assemblies 160a and 160b are their respective Detector Assemblies 162a and 162b. FIG. 25 also shows the positioning of the first and second Infrared Laser Assemblies 164a and 164b, and their respective Detector Assemblies 166a and 166b are also about 180 degrees on the opposing side of the patient space 112. The internal diameters of the rotatable mounts allow the respective internal diameters of the model to be either 25 or 36 inches. There are three bearing surfaces that allow for the rotatable mounts to be held in position yet still rotate.

Figure 26:
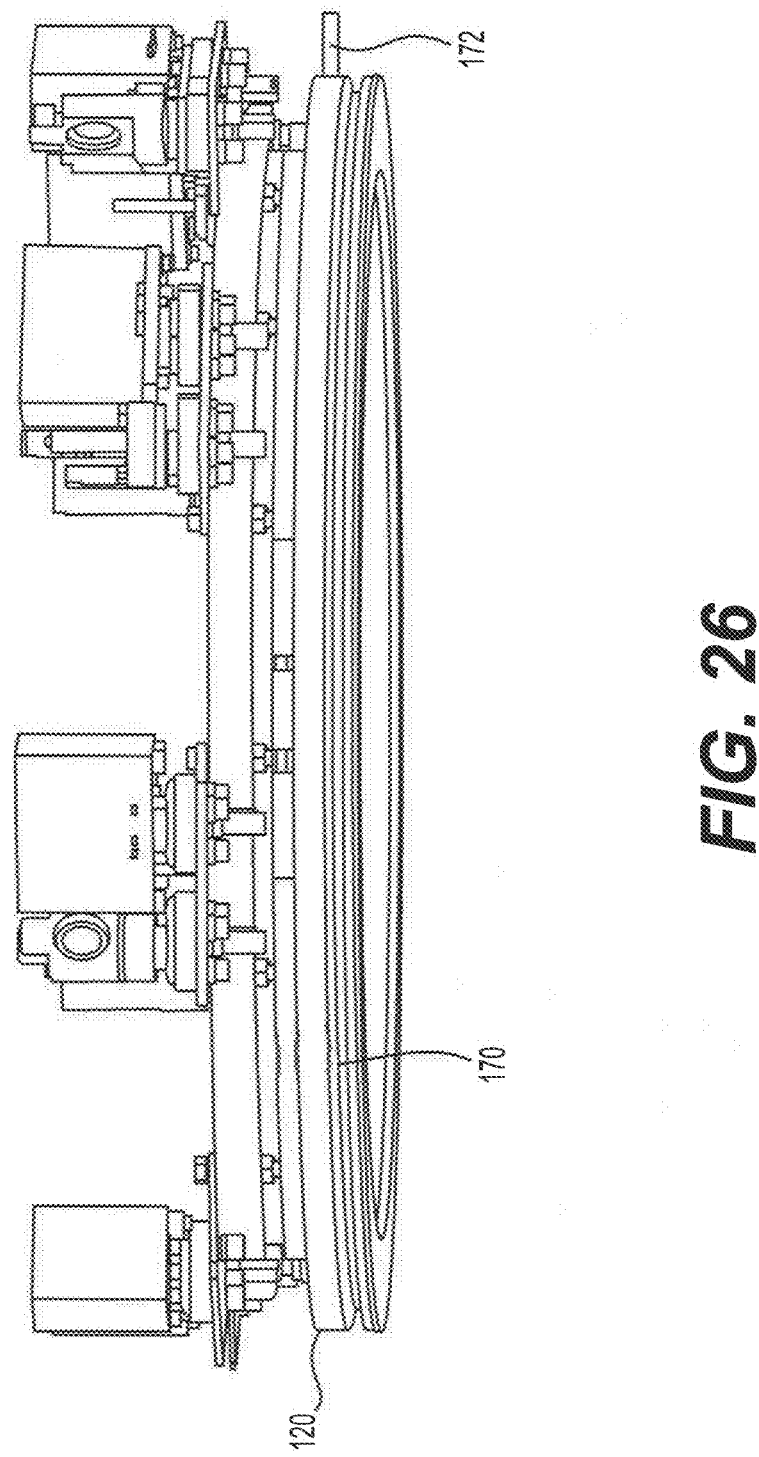
FIG. 26 is a front perspective view of the rotatable mount in FIG. 25.
Figure 27:
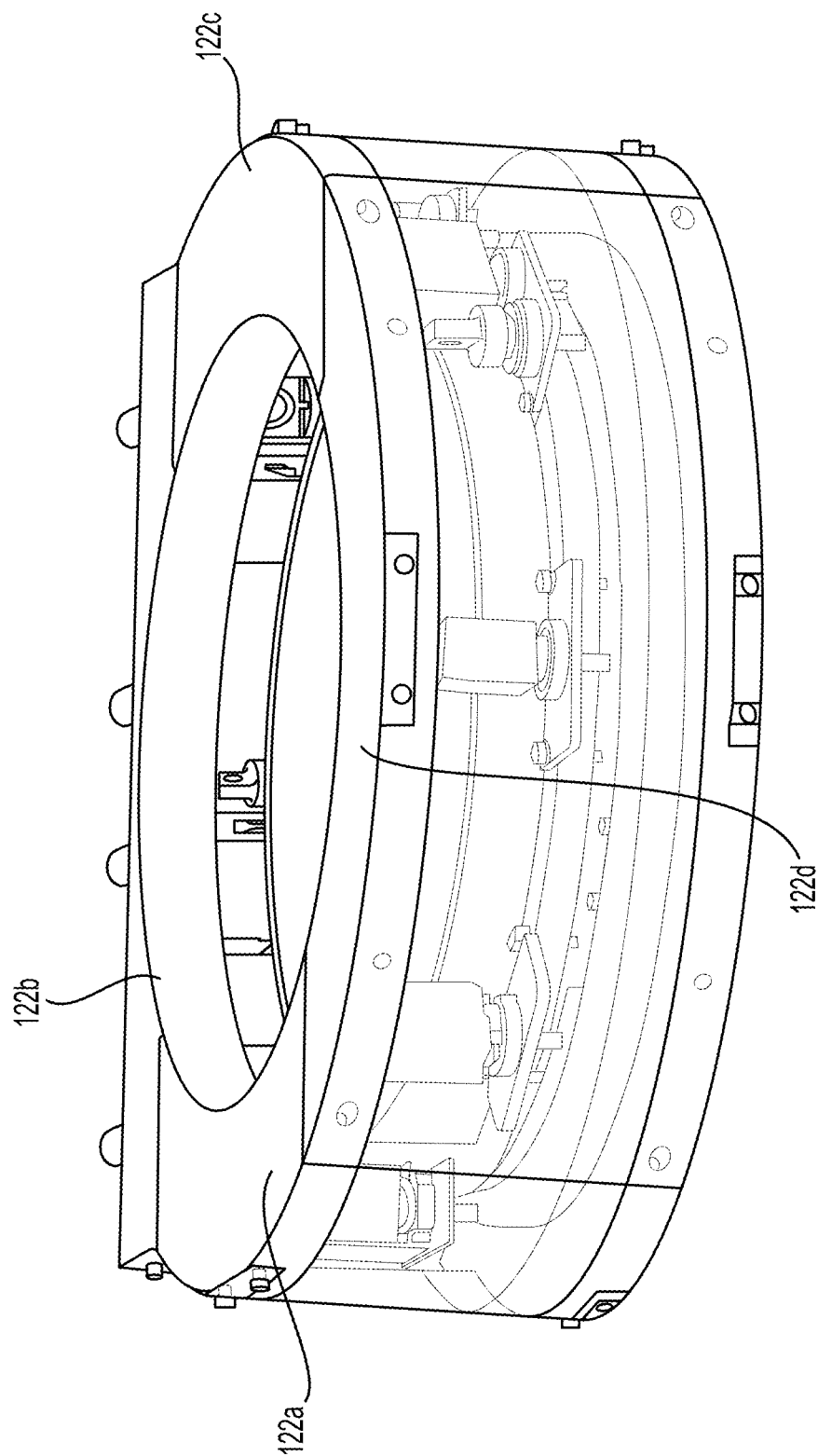
FIG. 27 is a front perspective view of a rotatable mount housing assembled from four quadrants in accordance with one embodiment.
Figure 28:
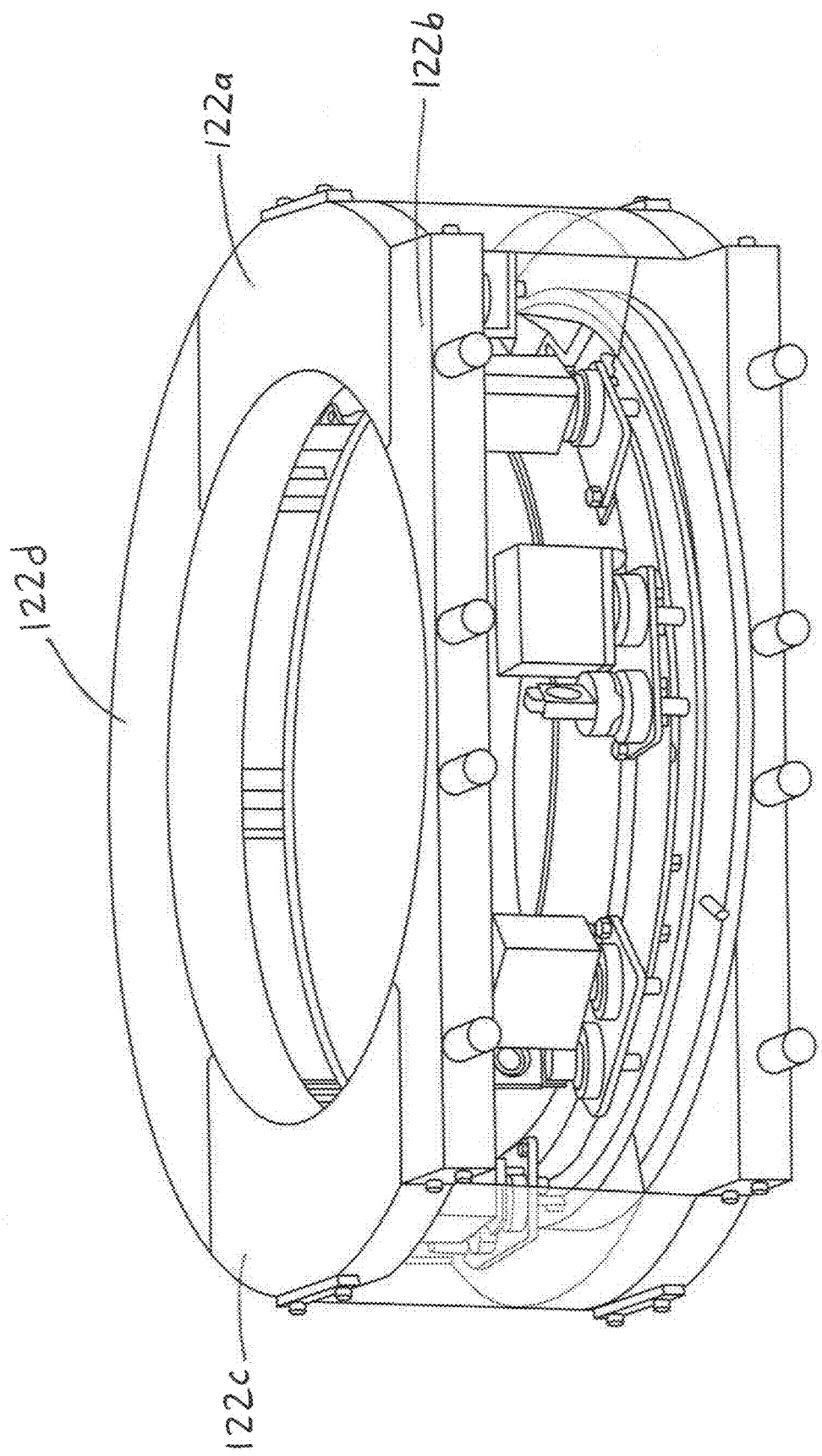
FIG. 28 is a rear perspective view of the rotatable mount housing in FIG. 27.

FIG. 26 shows that the ring 120 has a groove 170 that accommodates a standard V-belt the same size that is shown previously in the electric motor's sheave within the Imaging Head 130. At the right is a dowel 172 that provides an indication of the end of the rotatable mount's rotation. Also shown is the fact that both the fluorescent confocal rays and the infrared rays are used in a confocal fashion using beam splitters as shown previously in FIG. 1. The ring 120 and ring housing 122 may be segmented into four parts 122a, 122b, 122c and 122d for disassembly for travel held together by four socket head cap screws, as seen in FIGS. 27 and 28.

Figure 29:
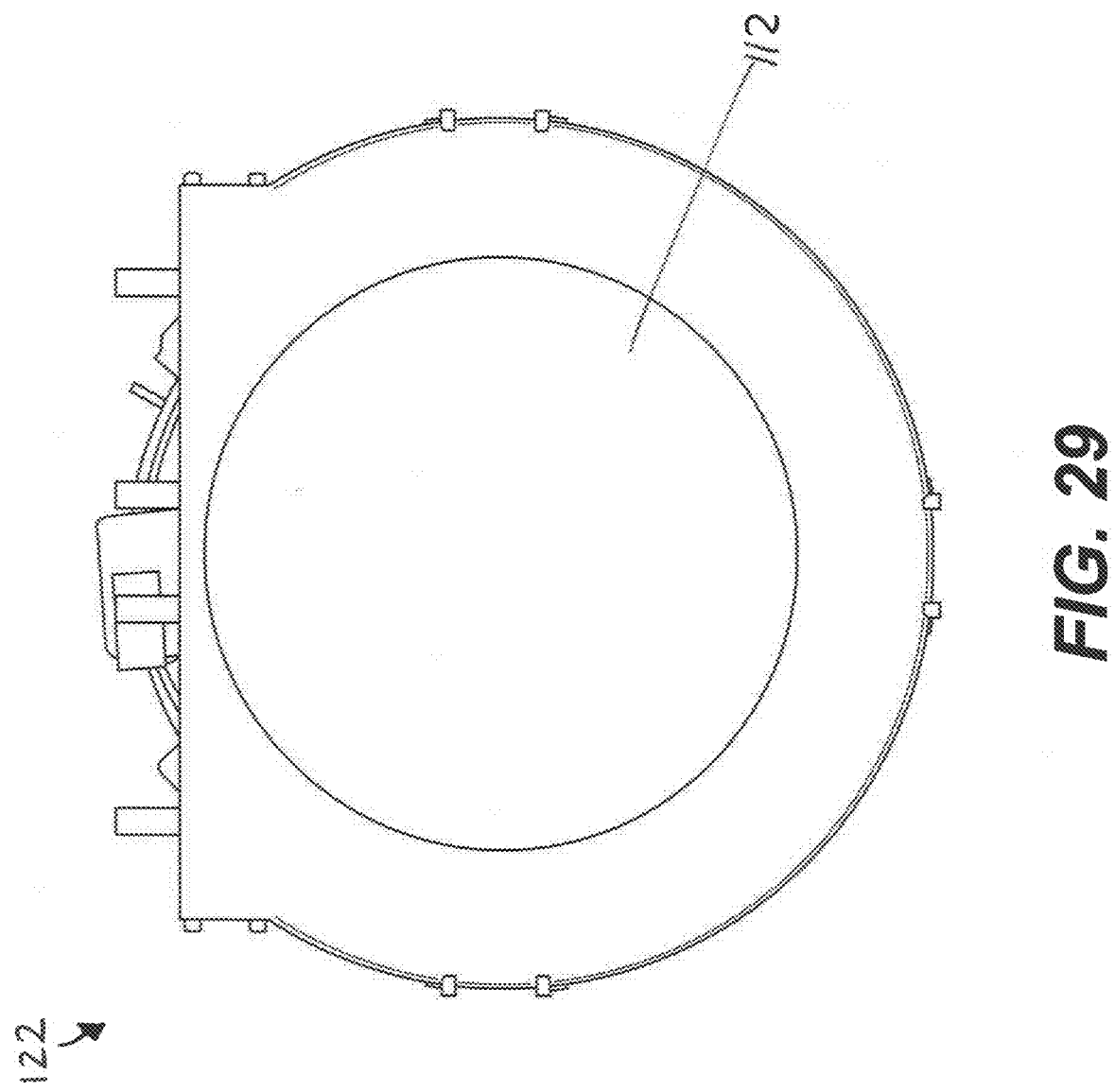
FIG. 29 is a top elevational view of the rotatable mount housing in FIG. 27.

FIG. 29 shows that there is no protrusion of any rotational parts into the space that the patient is in during use. The internal diameter of the embodiment shown is about 25 inches. In another embodiment, the internal diameter is about 36-inches.

Figure 30:
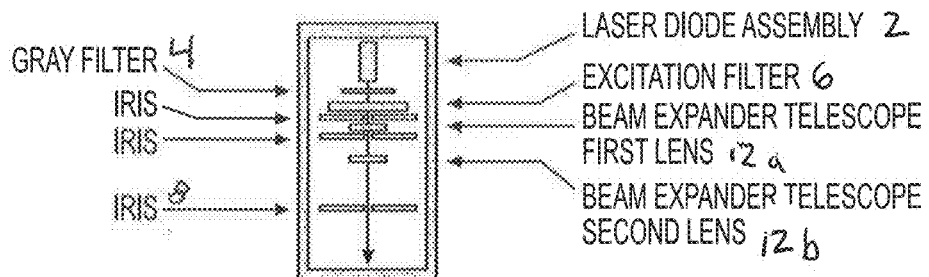
FIG. 30 is a schematic of a laser diode and excitation assembly in accordance with one embodiment.
Figure 31:
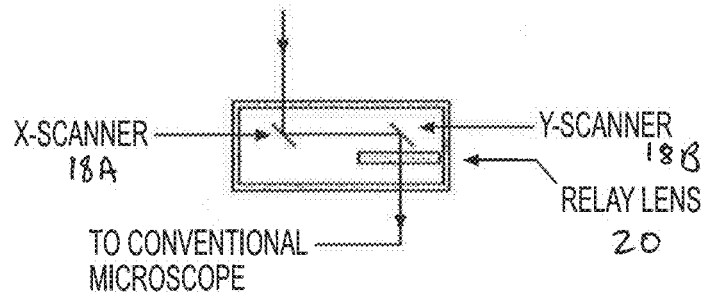
FIG. 31 is a schematic of a scanning assembly comprised of a X-scanner and a Y-scanner in accordance with one embodiment.
Figure 32:
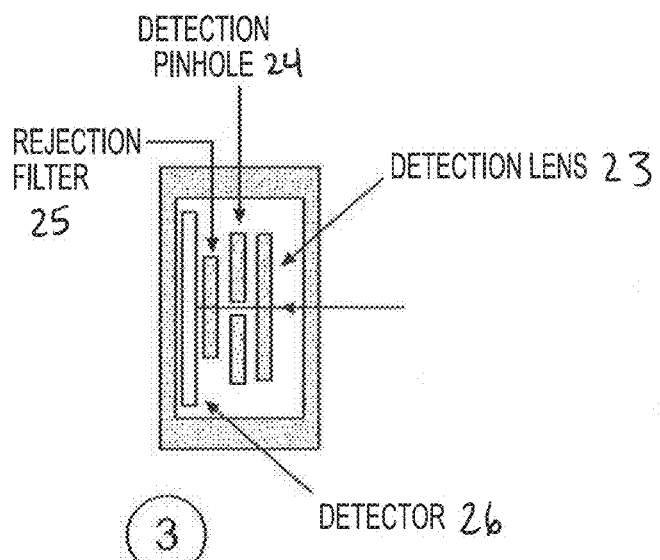
FIG. 32 is a schematic of a detector assembly in accordance with one embodiment.

FIG. 30 illustrates a concept used with both the fluorescent confocal rays as well as the infrared or near infrared rays used in a confocal microscopy fashion. As shown in FIG. 1, each ray passes through a beam splitter before passing through the patient and then on to the detector. A set of grey filters 4 is used to attenuate the laser power emitted from the laser diode assembly 2 and an excitation filter 6 selects a single line to emit through iris 8. The beam is expanded in the telescope (using beam expander telescope first and second lenses 12a and 12b, respectively) and spatially filtered with a pinhole 14. FIG. 31 illustrates the internals of an X-Y scanner as shown in FIG. 16. The beam splitter 16 deflects the expanded beam towards a scanner unit (comprising x-scanner 18a and y-scanner 18b) and the relay lens 20 focuses the beam into the primary image plane of the attached conventional microscope 22. FIG. 32 illustrates a detector assembly in accordance with one embodiment. The emitted fluorescent light is "descanned," passes the beam splitter 16, is focused into a pinhole 24 and detected with a photomultiplier 26 as a function of the scanner tilt angles. The two irises define the optical path of the instrument.

Figure 33:
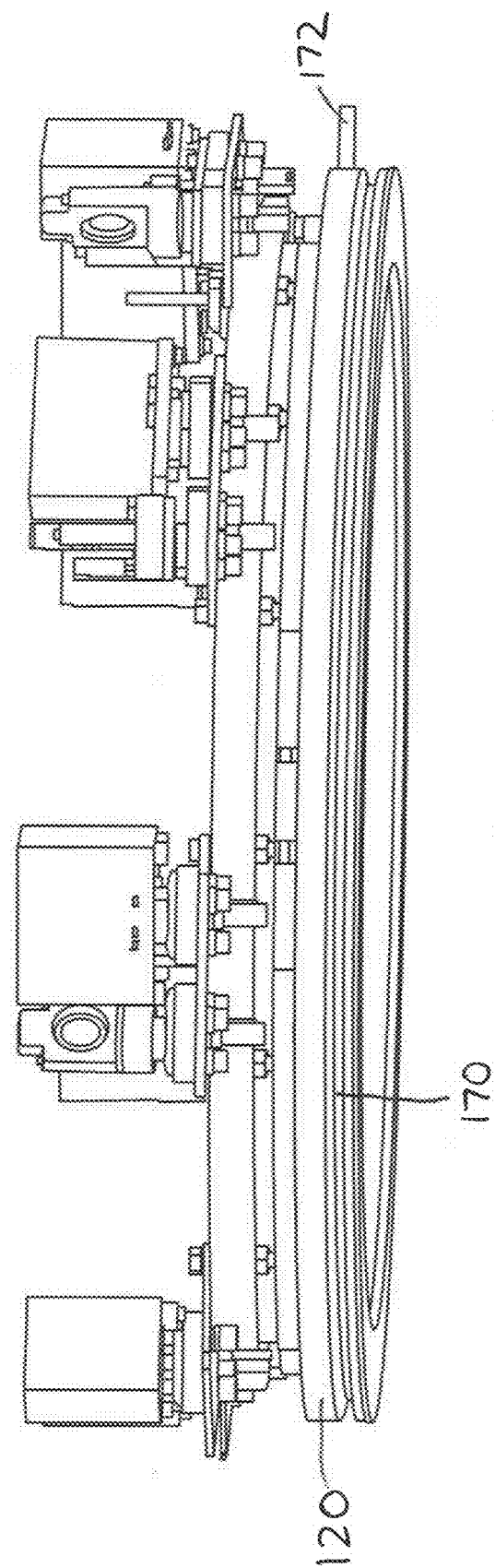
FIG. 33 is a front perspective view of a rotatable mount.
Figure 34:
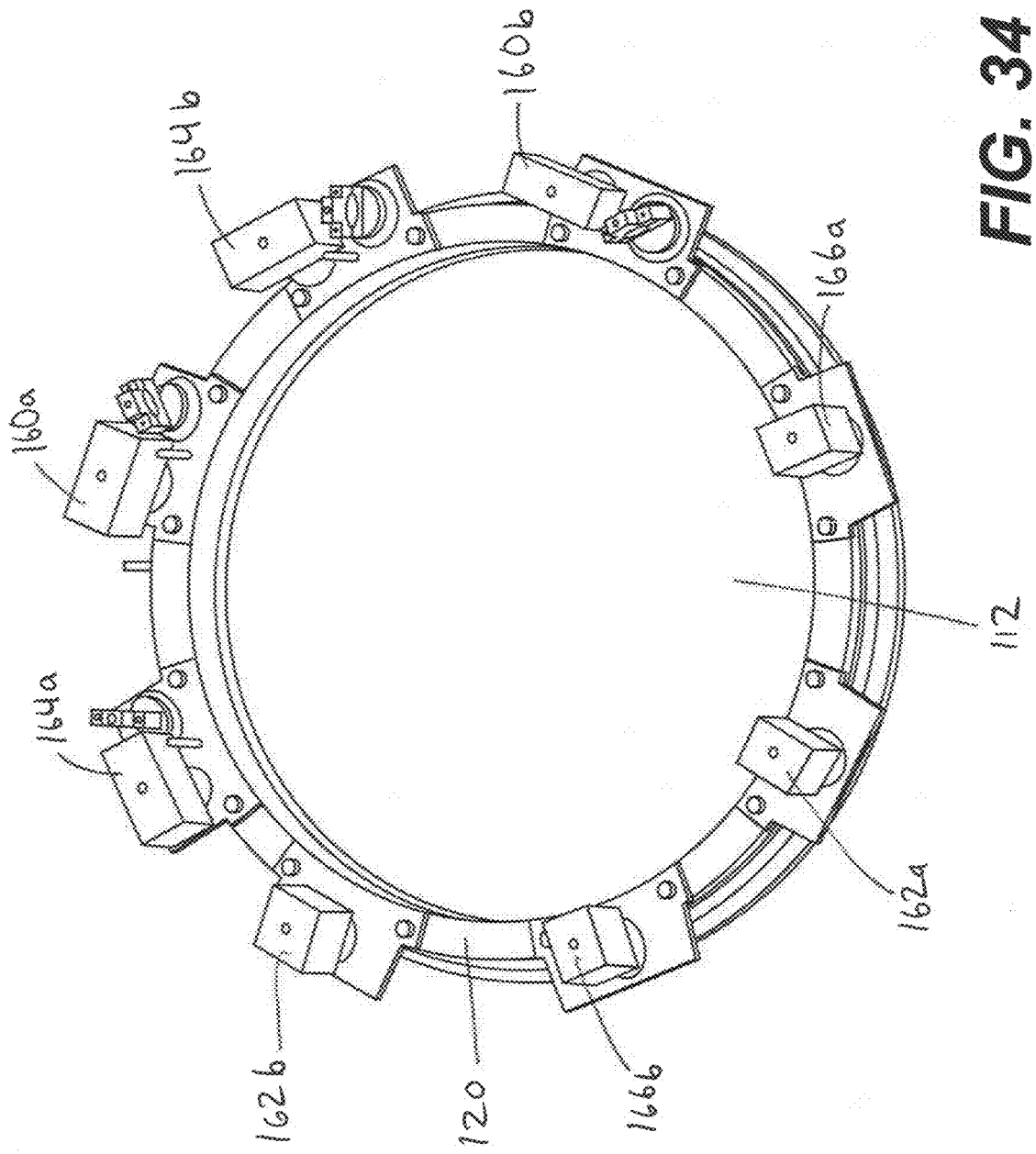
FIG. 34 is a top perspective view of the rotatable mount in FIG. 33.

FIG. 33 shows the V-belt groove on the rotatable mount 120 to provide rotational motion to the rotatable mount 120, but alternative embodiments may have a gearing option. The dowel 172 at the bottom right prompts a proximity sensor when a complete rotation is achieved. The front shows two confocal ray assemblies, one on the right in black (infrared ray), and one in grey on the left (fluorescent confocal ray). Both the fluorescent confocal ray and the infrared ray are treated in a fluorescent confocal microscopy fashion which includes a beam splitter where one is shown just to the left of the fluorescent confocal assembly of the discussion. The far left of the picture shows a Detection Assembly which sends Fourier Transform digital image signals to the PLC via the wireless slip-ring. The assemblies are fastened to the top surfaces of the rotatable mount by pre-loaded cap screws. The top of the rotatable mount has multiple levels, which allows each separate ray to have its own level so that flesh is not harmed by too much energy at one particular spot. FIG. 34 provides an overhead view.

Figure 35:
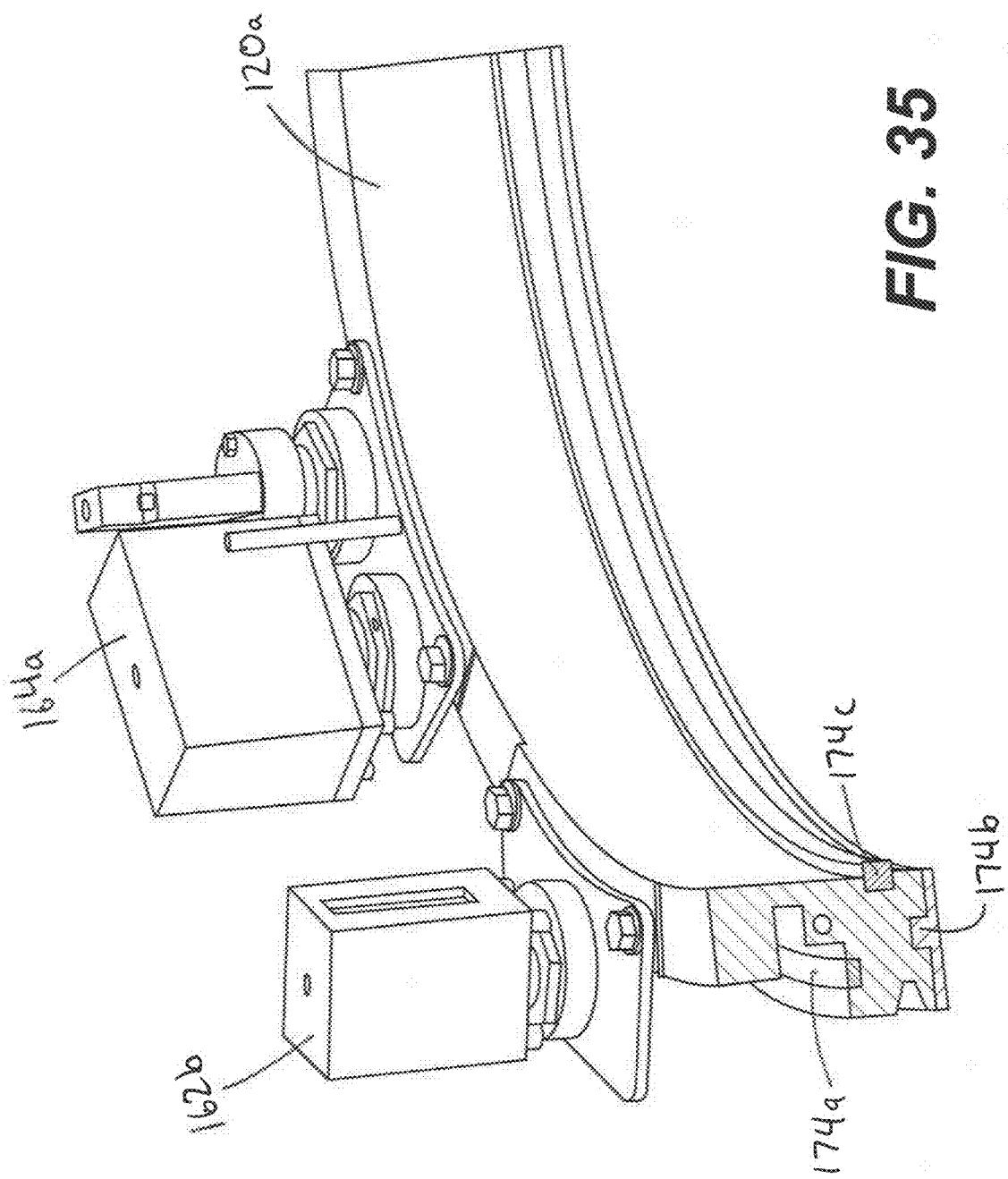
FIG. 35 is an enlarged perspective view of a quadrant of a rotatable mount in accordance with one embodiment.

FIG. 35 shows a quadrant 120a of the rotatable mount 120 according to one embodiment. For portability, the rotatable mount 120 may be segmented into quadrants. The quadrants are held together by four socket head cap screws. Sliding surfaces 174a, 174b, and 174c are provided on the rotatable mount 120 and coated with a dry lubricant coating. Underneath the confocal pieces are two confocal nuts that have holes for lock-wire. The confocal nuts of each rotatable mount quadrant are lock-wired together to prevent backing off of the confocal nuts.

Figure 36:
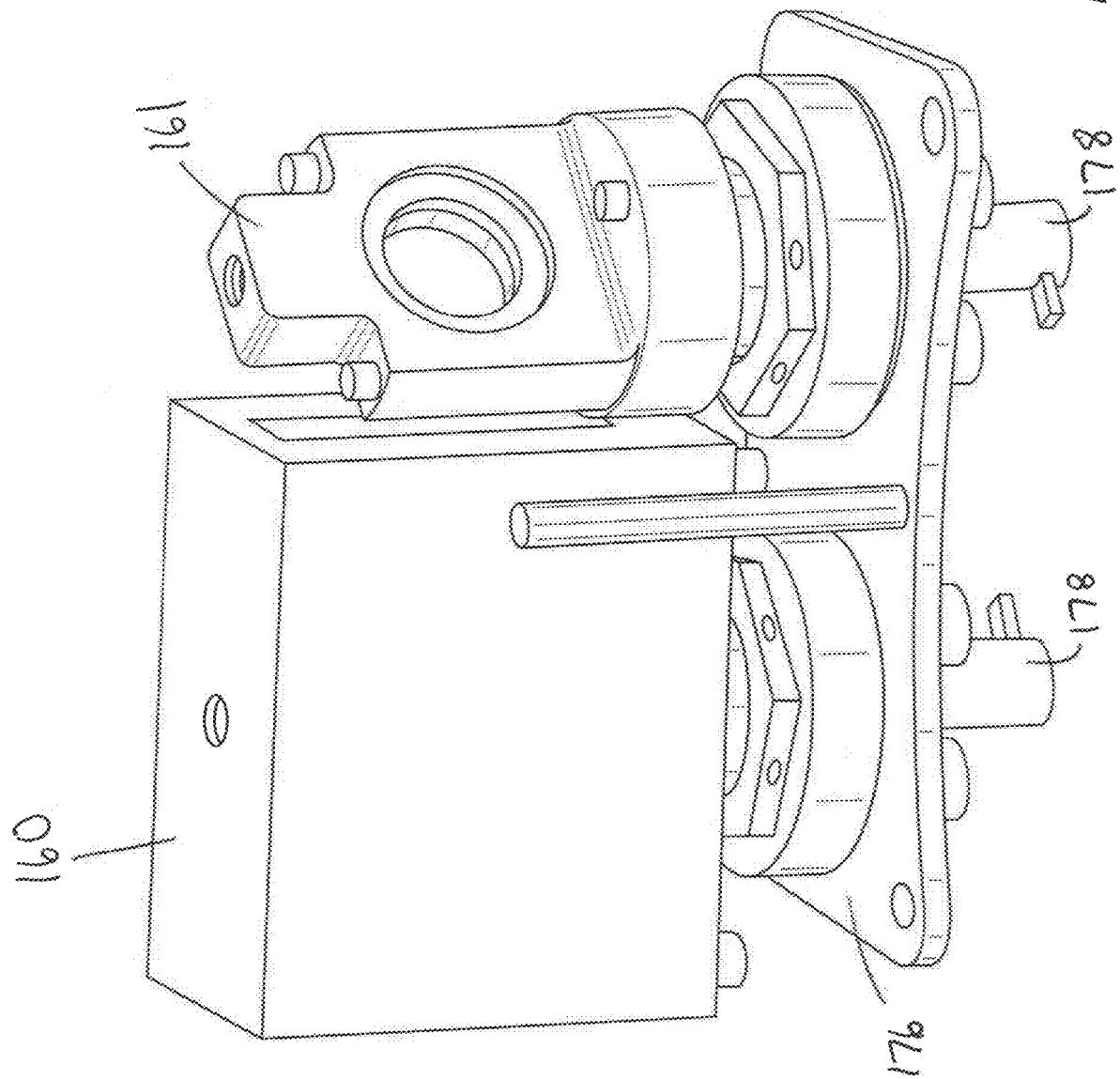
FIG. 36 is a front perspective view of a fluorescent confocal assembly in accordance with one embodiment.

FIG. 36 is an enlarged view showing that underneath the base plate 176 both the fluorescent confocal ray assembly 160 and the beam splitter 161 have 9V-0.5 A motors 178 that rotate to position the ray toward the detector 162. The motors 178 respond to the program which has a section that goes through a tuning process which directs the rays toward their respective detector irises. The lasers and each iris have a receiving antenna receive messages via the wireless slipring that allow for each iris to be adjusted.

Figure 37:
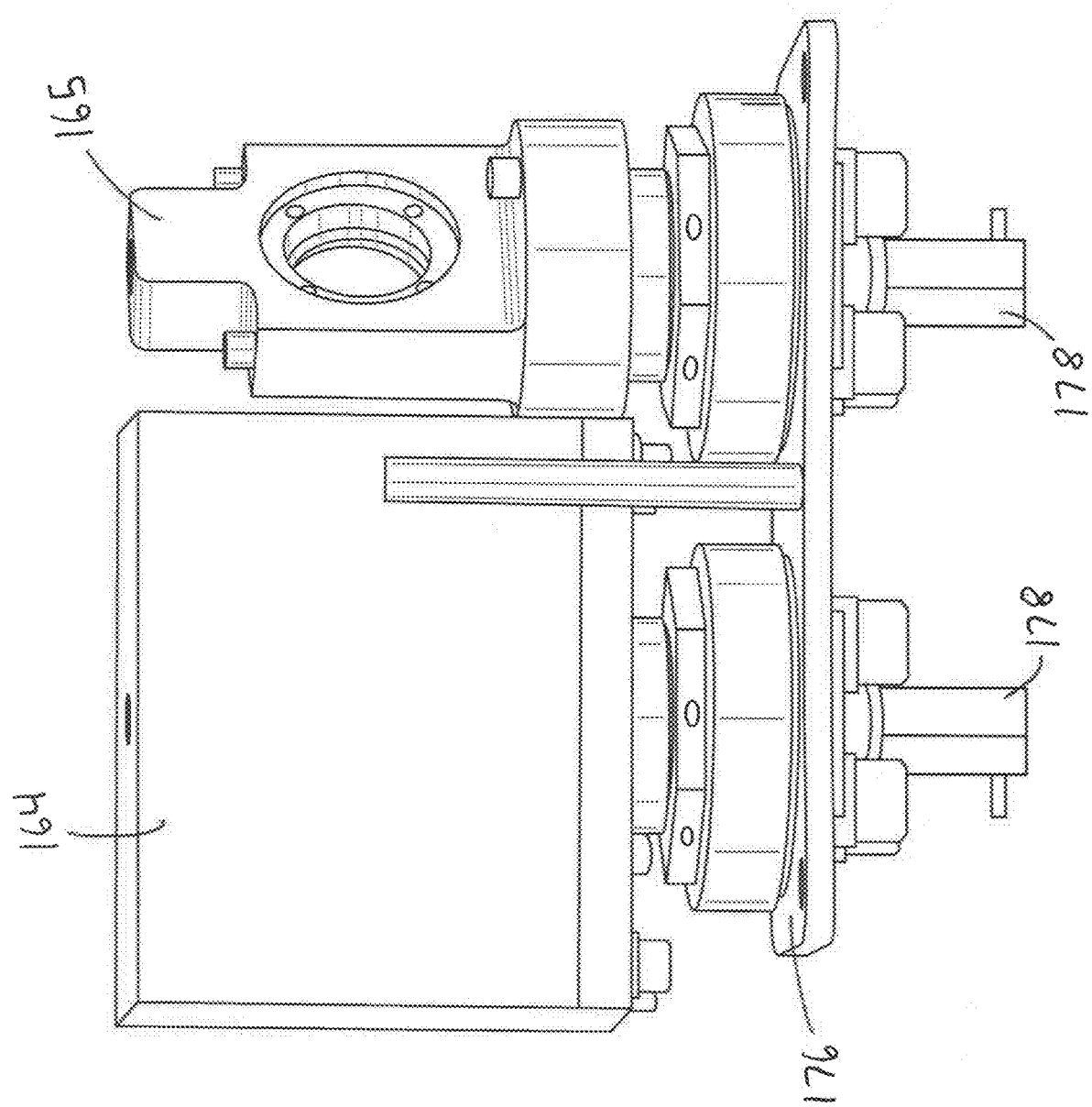
FIG. 37 is a front perspective view of an infrared confocal assembly in accordance with one embodiment.

FIG. 37 is an enlarged view showing the infrared confocal assembly 164 and its respective beam splitter 165 mounted onto a base 176 with motors 178 that rotate the infrared confocal assembly 164 and beam splitter 165. Both the fluorescent confocal and infrared confocal lasers will be operated at the $TEM_{00}$ mode. The wavelengths may range between about 500-950 nm. One example of a laser diode source compatible with the imaging system is HPD1005-9MM (Intense Ltd., North Brunswick, N.J.).

Figure 38:
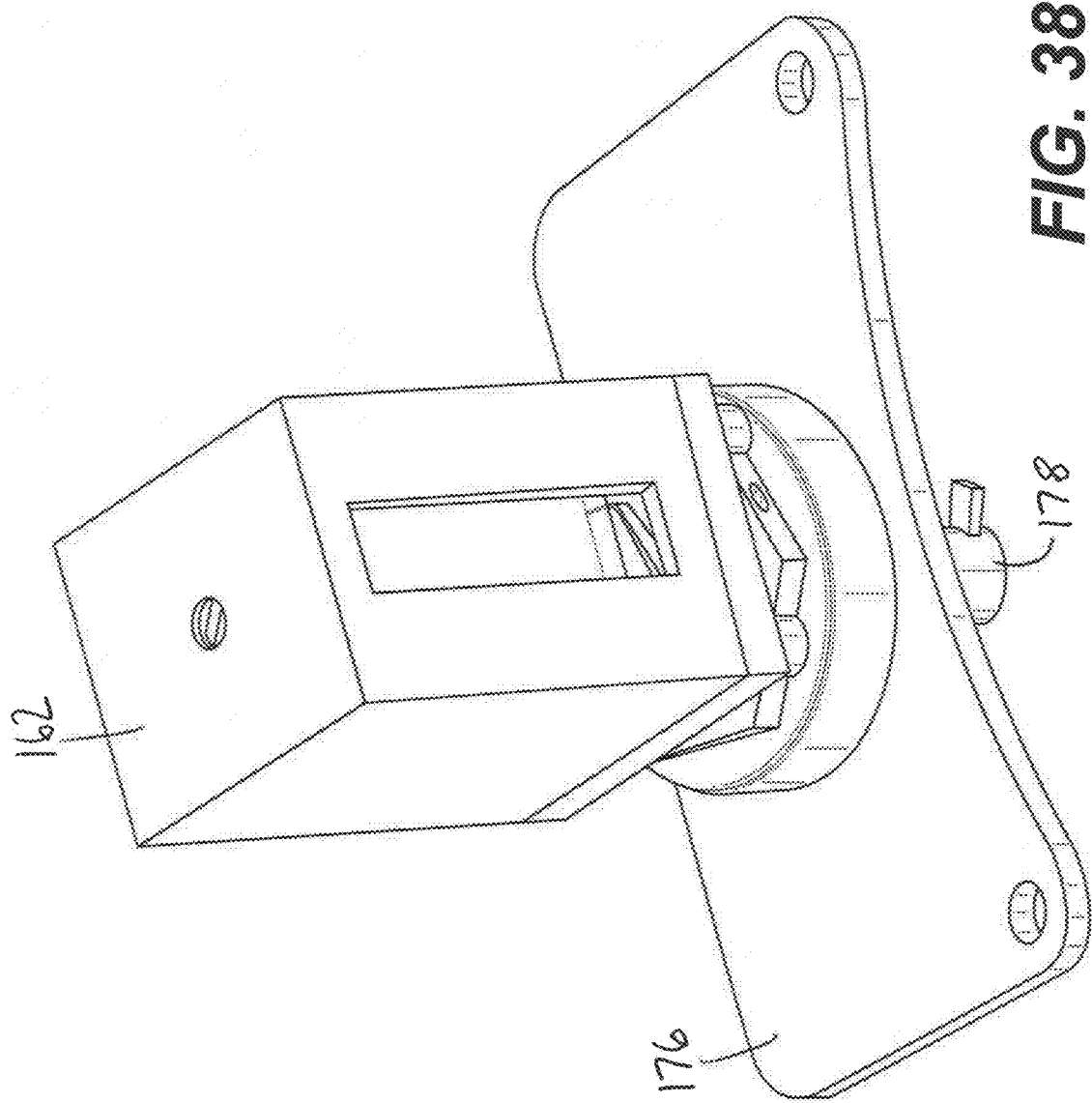
FIG. 38 is an overhead perspective view of a detector assembly in accordance with one embodiment.

FIG. 38 depicts one embodiment of a detector assembly 162 mounted onto a base 176 and rotated via a motor 178. The detector assembly uses the parts shown in FIG. 1 or a photomultiplier that either has a Charge-Coupled Device (CCD) within the photomultiplier or has a CCD within the detector assembly that converts the analog signals from the photomultiplier to digital signals that are then sent via a wireless antenna within the assembly to a wireless slip-ring that transmits the signal and associated level information to the immediate data storage part of the PLC that at the end of each rotation transmits the immediately stored data to the CPU image processing program. One example of a CCD adapted for use with the detector assembly 162 is a PI-SCX 7495-0002 (Roper Scientific, Trenton N.J.). The Fourier Transform signals sent by the detector assemblies are grey-scale arrays, when combined with the Fourier Transform signals of the perpendicular detector assembly within the CPU imaging program form voxels (digital volume with length×width×height measurements) which will have two different grey-scales produce by each Fourier Transform array of which those grey scales will be averaged to give each voxel its own specific grey-scale.

Each laser beam has its own level so that the other beams will not be affected traveling through the flesh, which is provided by raised surfaces on the rotatable mount. Currently, the proximity sensor will end the rotational data storage at the ($\pi$/2) position where a dowel is placed at the bottom of the rotatable mount. The two types of beams each have perpendicular beams to each other, but the beam type pairs are rotated from each other a certain number of degrees to allow for attachment of the confocal assemblies to the rotatable mount. The imaging program in its image alignment will calculate rotation of the specific images to align them together and overwrite one on top of the other. The total image will be translucent except for the portions of the image that correspond to suspect areas of a patient in order to show a physician or veterinarian where further consideration needs to be taken. The image also will show if a portion of the body has an elevated temperature over other areas of the body.

The combination of infrared and fluorescent microscopy assemblies provides a non-invasive means for obtaining sensitive, specific and high-resolution three-dimensional images at a target area of a subject. Using infrared wavelengths permits relatively deep photon penetration into tissue, minimal autofluorescence, less scatter and high optical contrast with fluorophores. There is a need to image tissues without the use of nuclear mediums. Systems such as MRIs, CT scans, and PET scans will reveal areas that could be cancerous growths, but one issue not addressed by such systems is identifying malignant tumors and distinguishing them from benign ones, particularly at regions containing multiple growths. Malignant tumors can have a +/−2° F. temperature difference from the surrounding tissue due to the different blood vessel patterns within the malignant tumor, and the grey-scale comparison in the CPU program of the imaging system is capable of identifying such differences. The program comparison is also adapted to identify areas of the subject that are below normal living temperature, which would indicate the possibility of necrosis.

Moreover, the portable nature of the imaging system enables the above benefits to be provided to remote locations having no local imaging facilities. In one embodiment, the imaging system has a vertical space envelope of 41.5"×39.5"×68.5" and a horizontal space envelope of 70.5"×47.5"×58". These dimensions may vary in other embodiments, provided that the imaging system remains portable.

Embodiments of the imaging system may have memory to store several images to allow speeding up the process if there is a need. Also, the electronic materials may be capable of withstanding all environmental conditions without the need of cooling. There may be an uninterruptible power supply (UPS) located at the side of the Stepper Motor. Embodiments of the machine may have an associated power converter for different power grids so that the machine may be able to operate in all power grids. To accommodate all grid locations, there may be an associated solar panel to use that provides ample electricity if no power grid is available.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

What is claimed is:

1. An imaging system for producing a three-dimensional image of a subject along a longitudinal y-axis and a cross section along x-z axes, the system comprising:
   (i) an image processing system having a memory and a computer processor;
   (ii) a plurality of imaging elements comprising:
      (a) a first confocal fluorescent microscopy assembly comprising a first fluorescent laser emitting a first incident light, a first beam splitter to receive the first incident light and to direct a first transmission portion along a first optical path, a first optical filter in operable engagement with the first transmission portion and delivering a first filtered transmission portion along a first optical path to a first photomultiplier or CCD;
      (b) a second confocal fluorescent microscopy assembly comprising a second fluorescent laser emitting a second incident light, a second beam splitter to receive the second incident light and to direct a second transmission portion along a second optical path, a second optical filter in operable engagement with the second transmission portion and delivering a second filtered transmission portion along a second optical path to a second photomultiplier or CCD;
      (c) wherein the first and second beam splitters and the first and second optical filters are chosen to match one or more predetermined fluorophores;
      (d) a first thermographic assembly comprising a first thermographic camera;
      (e) a second thermographic assembly comprising a second thermographic camera;
   (iii) a rotatable and longitudinally extensible mount disposed about the y-axis of the subject, the plurality of imaging elements engaged with the mount, wherein the first and second confocal fluorescent microscopy assemblies are engaged with the mount in relative orthogonal geometry about the subject so that the first and second optical paths cross at the y-axis and are configured to generate image data of the subject, and wherein the first and second thermographic assemblies are engaged with the mount in relative orthogonal geometry about the subject so as to be configured to image the subject with crossing thermally optical paths;
   (iv) a proximity sensor on the mount for determining an orientation value of the mount;

(v) wherein the mount is configured to rotate the imaging elements engaged with the mount relatively about the y-axis of the subject, the mount further configured to move the imaging elements engaged with the mount relatively along the y-axis of the subject, whereby the first and second confocal fluorescent microscopy assemblies are rotatable and extensible about the subject in consistent relative geometry and the first and second thermographic assemblies are rotatable and extensible about the subject in consistent relative geometry;

(vi) a controller in communication with the image processing system and the proximity sensor, the controller configured to receive the orientation value of the mount from the proximity sensor and control such rotational and extensible movement of the mount and to communicate a rotational and extension value to the image processing system;

wherein the image processing system is in operable communication with the first and second fluorescent microscopy assemblies, the first and second photomultipliers or CCDs configured to communicate digital image values to the image processing system;

wherein the image processing system is in operable communication with the first and second thermographic assemblies, the first and second thermographic cameras configured to communicate digital thermal image values to the image processing system; and wherein the computer processor of the image processing system is specifically configured so as to process digital image values from the first and second photomultipliers or CCDs, digital thermal image values from the first and second thermal cameras, with both in correlated association with the orientation value and the relative rotational and extension value from the controller so as to generate a three-dimensional voxel of the subject from rotational and extensible movement of the mount about the subject, the three-dimensional voxel having spatially associated thermal data.

2. The imaging system of claim 1, wherein the mount is ring-shaped.

3. The imaging system of claim 1, wherein the mount longitudinally extends along a vertical axis.

4. The imaging system of claim 3, wherein the mount has an internal diameter of 25 inches.

5. The imaging system of claim 1, wherein the mount longitudinally extends along a horizontal axis.

6. The imaging system of claim 5, wherein the mount has an internal diameter of 36 inches.

7. The imaging system of claim 1, wherein the mount is configured to rotate imaging elements engaged with the mount assembly via an electrically motorized gearing or a V-belt.

8. The imaging system of claim 1, wherein the mount is configured to move imaging elements engaged with the mount relatively along the y-axis via an electrically powered lead screw powered by a stepper motor.

9. The imaging system of claim 1 further including a tachometer in communication with the controller and the proximity sensor, wherein the tachometer is configured to measure a rotational speed of the mount and imaging elements and provide the rotational speed to the controller.

10. The imaging system of claim 9 wherein the proximity sensor comprises a dowel on the mount in communication with the controller and configured to provide the controller with the orientation value of the mount, wherein the dowel sends an electrical impulse to the controller to move the mount a set rotation and adjust the rotational speed of the mount.

11. The imaging system of claim 9 further including a brake configured to lower the rotational speed of the mount and the plurality of imaging elements engaged with the mount.

12. The imaging system of claim 1, wherein the fluorophore is indocyanine green dye.

13. The imaging system of claim 12, wherein the first and second fluorescent microscopy assemblies and the first and second thermographic assemblies are operated at a TEM00 mode.

14. The imaging system of claim 13, wherein the first and second fluorescent lasers emit the first and second incident light at a wavelength between 500 nm to 950 nm.

15. The imaging system of claim 13, wherein the first and second thermographic assemblies emit an infrared light at a wavelength between 700 nm to 950 nm.

16. An imaging system for producing a three-dimensional image of a subject along a longitudinal y-axis and a cross section along x-z axes, the system comprising:

(i) an image processing system having a memory and a computer processor;

(ii) a plurality of imaging elements comprising:

(a) a first confocal fluorescent microscopy assembly comprising a first fluorescent laser emitting a first incident light, a first beam splitter to receive the first incident light and to direct a first transmission portion along a first optical path, a first optical filter in operable engagement with the first transmission portion and delivering a first filtered transmission portion along a first optical path to a first photomultiplier or CCD;

(b) a second confocal fluorescent microscopy assembly comprising a second fluorescent laser emitting a second incident light, a second beam splitter to receive the second incident light and to direct a second transmission portion along a second optical path, a second optical filter in operable engagement with the second transmission portion and delivering a second filtered transmission portion along a second optical path to a second photomultiplier or CCD;

(c) wherein the first and second beam splitters and the first and second optical filters are chosen to match one or more predetermined fluorophores;

(d) a first thermographic assembly comprising a first thermographic camera;

(e) a second thermographic assembly comprising a second thermographic camera;

(iii) a rotatable and longitudinally extensible mount assembly disposed about the y-axis of the subject comprising a base having a lead screw extending along the y-axis and a ring-shaped mount adapted to move along the lead screw, the plurality of imaging elements engaged with the mount, wherein the first and second confocal fluorescent microscopy assemblies are engaged with the mount assembly in relative orthogonal geometry about the subject so that the first and second optical paths cross at the y-axis and are configured to generate image data of the subject, and wherein the first and second thermographic assemblies are engaged with the mount assembly in relative orthogonal geometry about the subject so as to be configured to image the subject with crossing thermally optical paths;

(iv) a proximity sensor on the mount assembly for determining an orientation value of the mount assembly;

(v) wherein the mount assembly is configured to rotate the imaging elements engaged with the mount relatively about the y-axis of the subject, the mount assembly further configured to move the imaging elements engaged with the mount assembly relatively along the y-axis of the subject, whereby the first and second confocal fluorescent microscopy assemblies are rotatable and extensible about the subject in consistent relative geometry and the first and second thermographic assemblies are rotatable and extensible about the subject in consistent relative geometry;

(vi) a controller in communication with the image processing system and the proximity sensor, the controller configured to receive the orientation value of the mount assembly from the proximity sensor and control such rotational and extensible movement of the mount assembly and to communicate a rotational and extension value to the image processing system;

wherein the image processing system is in operable communication with the first and second fluorescent microscopy assemblies, the first and second photomultipliers or CCDs configured to communicate digital image values to the image processing system;

wherein the image processing system is in operable communication with the first and second thermographic assemblies, the first and second thermographic cameras configured to communicate digital thermal image values to the image processing system; and wherein the computer processor of the image processing system is specifically configured so as to process digital image values from the first and second photomultipliers or CCDs, digital thermal image values from the first and second thermal cameras.

17. The imaging system of claim 16, wherein the base and the mount are parallel and the lead screw assembly is vertically oriented, whereby the mount moves along a vertical axis.

18. The imaging system of claim 16, wherein the base and the mount are perpendicular and the lead screw assembly is horizontally oriented, whereby the mount moves along a horizontal axis.

* * * * *